US008263556B2

(12) United States Patent
Du Clos et al.

(10) Patent No.: US 8,263,556 B2
(45) Date of Patent: Sep. 11, 2012

(54) SUPPRESSIVE MACROPHAGES, C-REACTIVE PROTEIN AND THE TREATMENT OF SYSTEMIC LUPUS ERYTHEMATOSUS AND IMMUNE THROMBOCYTOPENIC

(75) Inventors: Terry W. Du Clos, Albuquerque, NM (US); Carolyn Mold, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 424 days.

(21) Appl. No.: 12/312,090

(22) PCT Filed: Nov. 6, 2007

(86) PCT No.: PCT/US2007/023311
§ 371 (c)(1),
(2), (4) Date: May 19, 2009

(87) PCT Pub. No.: WO2008/057505
PCT Pub. Date: May 15, 2008

(65) Prior Publication Data
US 2011/0142812 A1    Jun. 16, 2011

Related U.S. Application Data

(60) Provisional application No. 60/857,008, filed on Nov. 6, 2006.

(51) Int. Cl.
*A61K 38/00* (2006.01)
(52) U.S. Cl. .................. 514/13.5; 514/13.8; 514/1
(58) Field of Classification Search .................. None
See application file for complete search history.

(56) References Cited

U.S. PATENT DOCUMENTS
8,013,120 B2    9/2011    Du Clos et al.

OTHER PUBLICATIONS

Zhang et al. Eur. J. Immunol. 2006, 36:2993-3006.*
Attwood (Science 290: 471-473, 2000).*
Skolnick et al. (Trends in Biotech. 18: 34-39, 2000).*
Ogden et al., Single-Dose Therapy for Lupus Nephritis: C-Reactive Protein, Nature's Own Dual Scavenger and Immunosuppressant. Arthritis & Rheumatism 52:378-381 (2005).
Fidler, Therapy of Disseminated Melanoma by Liposome-Activated Macrophages. World J. Surg. 16:270-276 (1992).
Du Clos TW. Function of C-reactive protein. *Ann Med* 2000; 32:274-8.
Du Clos TW. The interaction of C-reactive protein and serum amyloid P component with nuclear antigens. *Mol Biol Rep* 1996; 23:253-60.
Volanakis JE. Human C-reactive protein: expression, structure, and function. *Mol Immunol* 2001;38:189-197.
Gabay C, Roux-Lombard P, de Moerloose P, Dayer J-M, Vischer T, Guerne P-A. Absence of correlation between interleukin 6 and C-reactive protein blood levels in Systemic Lupus Erythematosus compared with Rheumatoid Arthritis. J Rheumatol 1993;20:815-821.
Du Clos TW, Mold C. C-reactive protein: an activator of innate immunity and a modulator of adaptive immunity. *Immunol Res* 2004;30:261-78.
Heuertz RM, Dongyuan X, Samols D, Webster RO. Inhibition of C5a des Arg-induced neutrophil alveolitis in transgenic mice expressing C-reactive protein. *Am J Physiol*, 1994;266:L649-L654.
Heuertz RM, Piquette CA, Webster RO. Rabbits with elevated serum C-reactive protein exhibit diminished neutrophil infiltration and vascular permeability in C5a-induced alveolitis. *Am J Pathol* 1993;142:319-328.
Xia D, Samols D. Transgenic mice expressing rabbit C-reactive protein are resistant to endotoxemia. *Proc Natl Acad Sci USA* 1997;94:2575-80.
Mold C, Rodriguez W, Rodic-Polic B, Du Clos TW. C-reactive protein mediates protection from lipopolysaccharide through interactions with Fc gamma R. *J Immunol* 2002;169:7019-25.
Szalai AJ, Nataf S, Hu X-Z, Barnum SR. Experimental allergic encephalomyelitis is inhibited in transgenic mice expressing human C-reactive protein. *J Immunol* 2002;168:5792-5797.
Gershov D, Kim S, Brot N, Elkon KB. C-reactive protein binds to apoptotic cells, protects the cells from assembly of the terminal complement components, and sustains an antiinflammatory innate immune response: implications for systemic autoimmunity. *J Exp Med* 2000;192:1353-1363.
Mold C, Baca R, Du Clos TW. Serum amyloid P component and C-reactive protein opsonize apoptotic cells for phagocytosis through Fcγ receptors. *J Autoimmun* 2002;19:147-54.
Du Clos TW, Zlock LT, Hicks PS, Mold C. Decreased autoantibody levels and enhanced survival of (NZB x NZW) F1 mice treated with C-reactive protein. *Clin Immunol Immunopathol* 1994;70:22-7.
Szalai AJ, Weaver CT, McCrory MA, van Ginkel FW, Reiman RM, Kearney JF, Marion TN, Volanakis JE. Delayed lupus onset in (NZB x NZW)FI mice expressing a human C-reactive protein transgene. *Arthritis Rheum* 2003;48:1602-11.
Rodriguez W, Mold C, Kataranovski M, Hutt J, Marnell LL, Du Clos TV Reversal of ongoing proteinuria in autoimmune mice by treatment with C-reactive protein. *Arthritis Rheum* 2005;52:642650.
Theofilopoulos AN, Dixon FJ. Murine models of systemic lupus erythematosus. *Adv Immunol* 1985;37:269-391.

(Continued)

*Primary Examiner* — Sharon Wen
(74) *Attorney, Agent, or Firm* — Henry D. Coleman; R. Neil Sudol; William J. Sapone

(57) ABSTRACT

The present invention relates to the use of suppressive macrophage or dendritic cells (activated with C-reactive protein or CRP-related compounds), for the treatment of various disease states and conditions associated with immune thrombocytopenic purpura (ITP) and/or systemic lupus erythematosus (SLE), including lupus of the skin (discoid), systemic lupus of the joints, lungs and kidneys, hematological conditions including hemolytic anemia and low lymphocyte counts, lymphadenopathy and CNS effects, including memory loss, seizures and psychosis, among numerous others as otherwise disclosed herein. In another aspect of the invention, the reduction in the likelihood that a patient who is at risk for an outbreak of a disease state or condition associated with systemic lupus erythematosus or ITP will have an outbreak is an additional aspect of the present invention. In the case of ITP, methods of the present invention are used to increase platelet counts in the treated patient. In addition, in the case of ITP, the present invention relates to the use of CRP or a CRP-related compound in the absence of suppressive macrophages for the treatment of ITP.

14 Claims, 12 Drawing Sheets

OTHER PUBLICATIONS

Du Clos TW. C-reactive protein reacts with the U1 small nuclear ribonucleoprotein. *J Immunol* 1989;143:2553-9.

van Rooijen N, Sanders A. Liposome mediated depletion of macrophages: mechanism of action, preparation of liposomes and applications *J Immunol Methods* 1994;174:83-93.

Du Clos TW, Volzer MA, Hahn FF, Mao R, Mold C, Searles RP. Chromatin clearance in C57BU10 mice: interaction with heparan sulphate proteoglycans and receptors on Kupffer cells. *Clin Exp Immunol* 1999;117:403-11.

Oldenhove G, de Heusch M, Urbain-Vansanten G, Urbain J, Maliszewski C, Leo 0, Moser M. CD4+ CD25+ regulatory T cells control T helper cell type 1 responses to foreign antigens induced by mature dendritic cells in vivo. *J Exp Med* 2003;199:259-66.

Rubin RL. Enzyme-linked immunosorbent assay for anti-DNA and antihistone antibodies. In: Rose NR, Friedman H, Fahey JL, editors. Manual of Clinical Laboratory Immunology. Washington: ASM; 1986. p. 744-749.

Kikawada E, Lenda DM, Kelley VR. IL-12 deficiency in MRL-Faslpr) mice delays nephritis and intrarenal IFN-gamma expression, and diminishes systemic pathology. *J Immunol* 2003;170:3915-25.

Smeenk RJ, Brinkman K, van den Brink HG, Westgeest AA. Reaction patterns of monoclonal antibodies to DNA. *J Immunol* 1988;140:378692.

McHugh RS, Shevach EM. Cutting edge: depletion of CD4+CD25+ regulatory T cells is necessary, but not sufficient, for induction of organ-specific autoimmune disease. *J Immunol* 2002;168:597983.

Du Clos T V C-reactive protein as a regulator of autoimmunity and inflammation. *Arthritis Rheum* 2003; 48:1475-7.

Christensen SR, Kashgarian M, Alexopoulou L, Flavell RA, Akira S, Shlomchik MJ Toll-like receptor 9 controls anti-DNA autoantibody production in mirine lupus. *J Exp Med* 2005;202:321-331.

Zhou T, Bluethmann H, Eldridge J, Berry K, Mountz JD. Origin of CD4-CD8-B220+ T cells in MRL-lpr/lpr mice. Clues from a T cell receptor beta transgenic mouse. *J Immunol* 1993;150:3651-67.

Tesch GH, Maifert S, Schwarting A, Rollins BJ, Kelley VR. Monocyte chemoattractant protein 1-dependent leukocytic infiltrates are responsible for autoimmune disease in MRL-*Faslpr*) mice. *J Exp Med* 1999;190:1813-24.

Walport MJ. Lupus, DNase and defective disposal of cellular debris. *Nat Genet* 2000;25:1356.

Kim SJ, Gershov D, Ma X, Brot N, Elkon KB. Opsonization of apoptotic cells and its effect on macrophage and T cell immune responses. *Ann Ny Acad Sci* 2003;987:68-78.

Ehrenstein MR, Cook HT, Neuberger MS. Deficiency in serum immunoglobulin IgM predisposes to development of IgG autoantibodies. *J Exp Med* 2000;191:1253-8.

Boes M, Schmidt T, Linkemann K, Beaudette BC, Marshak-Rothstein A, Chen J. Accelerated development of IgG autoantibodies and autoimmune disease in the absence of secreted IgM. *Proc Natl Acad Sci USA* 2000;97:1184-9.

Botto M, Walport W. Clq, autoimmunity and apoptosis. *Immunobiology* 2002;205:395-406.

Clynes R, Dumitru C, Ravetch JV. Uncoupling of immune complex formation and kidney damage in autoimmune glomerulonephritis. *Science* 1998;279:1052-1054.

Balomenos D, Rumold R, Theofilopoulos AN. Interferon-gamma is required for lupus-like disease and lymphoaccumulation in MRL-lpr mice. *J Clin Invest* 1998;101:364-71.

Heuertz RM, Xia D, Samols D, Webster RD. Inhibition of C5a des Arg-induced neutrophil alveolitis in transgenic mice expressing C-reactive protein. *Am J Physiol* 1994;266:L649-L654.

Baltz ML, Rowe IF, Pepys MB. In vivo turnover studies of C-reactive protein. *Clin Exp Immunol* 1985;59:243-50.

Hutchinson WL, Noble GE, Hawkins PN, Pepys MB. The pentraxins, C-reactive protein and serum amyloid p. component, are cleared and catabolized by hepatocytes in vivo. *J Clin Invest* 1994;94:1390-1396.

Carvalho-Pinto CE, Garcia MI, Mellado M, Rodriguez-Frade JM, Martin-Caballero J, Flores J, Martinez AC, Balomenos D. Autocrine production of IFN-gamma by macrophages controls their recruitment to kidney and the development of glomerulonephritis in MRL/lpr mice. *J Immunol* 2002;169:1058-67.

Groux H, O'Garra A, Bigler M, Rouleau M, Antonenko S, de Vries JE, Roncarolo MG. A CD4+ T-cell subset inhibits antigen-specific T-cell responses and prevents colitis. *Nature* 1997;389:737-42.

Rodriguez, W., C. Mold, M. Kataranovski, J. Hutt, L. L. Marnell, and T. W. Du-Clos 2005. Reversal of ongoing proteinuria in autoimmune mice by treatment with C-reactive protein. *Arthritis Rheum* 52:642-650.

Rodriguez, W., C. Mold, L. L. Marnell, J. Hutt, G. J. Silverman, D. Tran, and T. W. Du-Clos. 2006. Prevention and reversal of nephritis in MRL/lpr mice with a single injection of C-reactive protein. *Arthritis Rheum* 54:325-335.

Siragam, V., A. R. Crow, D. Brinc, S. Song, J. Freedman, and A. H. Lazarus. 2006. Intravenous immunoglobulin ameliorates ITP via activating Fc © receptors on dendritic cells. *Nat Med* 12:688-692.

Marnell, L., C. Mold, and T. W. Du-Clos. 2005. C-reactive protein: ligands, receptors and role in inflammation. *Clin Immunol* 117:104-111.

Marnell, L. L., C. Mold, M. A. Volzer, R. W. Burlingame, and T. W. Du-Clos. 1995. C-reactive protein binds to FcγRI in transfected COS cells. *J Immunol* 155:2185-2193.

Bharadwaj, D., M. P. Stein, M. Volzer, C. Mold, and T. W. Du Clos. 1999. The major receptor for C-reactive protein on leukocytes is Fcγ receptor II. *J Exp Med* 190:585-590.

Bang, R et al.; Analysis of Binding Sites in Human C-reactive Protein for FcgammaRI, FcgammaRIA, and C1q by Site-directed Mutagenesis; J. Biol Chem.2005; 280:25095-25102.

\* cited by examiner

FIGURE 1

Complete CRP sequence (SEQ ID No: 1)

| | | | | | | | | | | |
|---|---|---|---|---|---|---|---|---|---|---|
| Gln | Thr | Asp | Met | Ser | Arg | Lys | Ala | Phe | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

D112N (SEQ ID No: 2)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asn | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Figure 1 (Cont'd)

D112A (SEQ ID No: 3)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Ala | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

H38R (SEQ ID No: 4)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | Arg | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Figure 1 (Cont'd)

D169A (SEQ ID No: 5)

| Gln | Thr | Asp | Met | Ser | Arg | Lys | Ala | Phe | Val | Phe | Pro |
|-----|-----|-----|-----|-----|-----|-----|-----|-----|-----|-----|-----|
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Ala | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Y175L (SEQ ID No: 6)

| Gln | Thr | Asp | Met | Ser | Arg | Lys | Ala | Phe | Val | Phe | Pro |
|-----|-----|-----|-----|-----|-----|-----|-----|-----|-----|-----|-----|
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Leu | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

Figure 1 (Cont'd)

L176Q (SEQ ID No: 7)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Phe | Trp | Ser | Lys | Asp | Ile | Gly |
| Tyr | Ser | Phe | Thr | Val | Gly | Gly | Ser | Glu | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Gln | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

F66A/E81A (Seq ID No: 8)

| | | | | | | | | | | | |
|---|---|---|---|---|---|---|---|---|---|---|---|
| Gln | Thr | Asp | Met | Ser | Arg | Lys | Ala | Phe | Val | Phe | Pro |
| Lys | Glu | Ser | Asp | Thr | Ser | Tyr | Val | Ser | Leu | Lys | Ala |
| Pro | Leu | Thr | Lys | Pro | Leu | Lys | Ala | Phe | Thr | Val | Cys |
| Leu | His | Phe | Tyr | Thr | Glu | Leu | Ser | Ser | Thr | Arg | Gly |
| Tyr | Ser | Ile | Phe | Ser | Tyr | Ala | Thr | Lys | Arg | Gln | Asp |
| Asn | Glu | Ile | Leu | Ile | Ala | Trp | Ser | Lys | Asp | Ile | Gly |
| Tyr | Ser | Phe | Thr | Val | Gly | Gly | Ser | Ala | Ile | Leu | Phe |
| Glu | Val | Pro | Glu | Val | Thr | Val | Ala | Pro | Val | His | Ile |
| Cys | Thr | Ser | Trp | Glu | Ser | Ala | Ser | Gly | Ile | Val | Glu |
| Phe | Trp | Val | Asp | Gly | Lys | Pro | Arg | Val | Arg | Lys | Ser |
| Leu | Lys | Lys | Gly | Tyr | Thr | Val | Gly | Ala | Glu | Ala | Ser |
| Ile | Ile | Leu | Gly | Gln | Glu | Gln | Asp | Ser | Phe | Gly | Gly |
| Asn | Phe | Glu | Gly | Ser | Gln | Ser | Leu | Val | Gly | Asp | Ile |
| Gly | Asn | Val | Asn | Met | Trp | Asp | Phe | Val | Leu | Ser | Pro |
| Asp | Glu | Ile | Asn | Thr | Ile | Tyr | Leu | Gly | Gly | Pro | Phe |
| Ser | Pro | Asn | Val | Leu | Asn | Trp | Arg | Ala | Leu | Lys | Tyr |
| Glu | Val | Gln | Gly | Glu | Val | Phe | Thr | Lys | Pro | Gln | Leu |
| Trp | Pro | | | | | | | | | | |

FIGURE 3A, B, C
3A
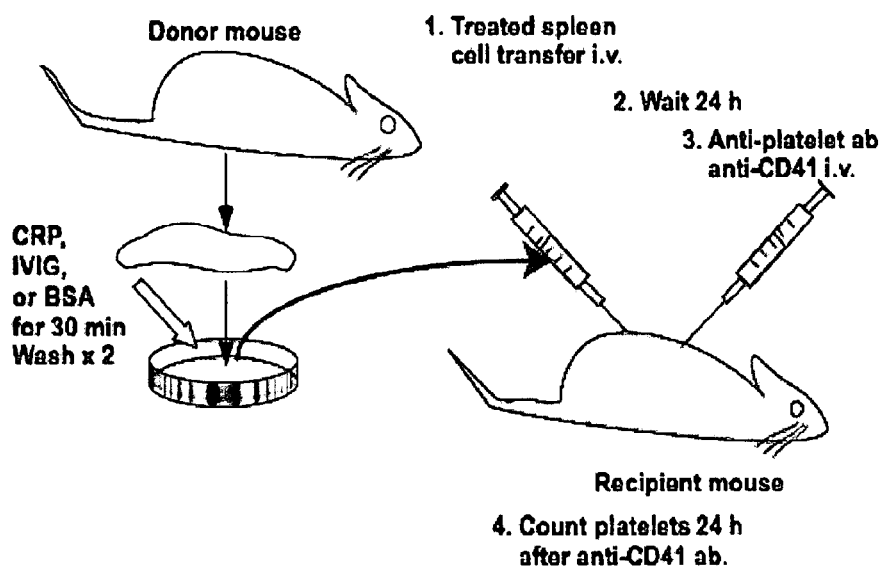
3B
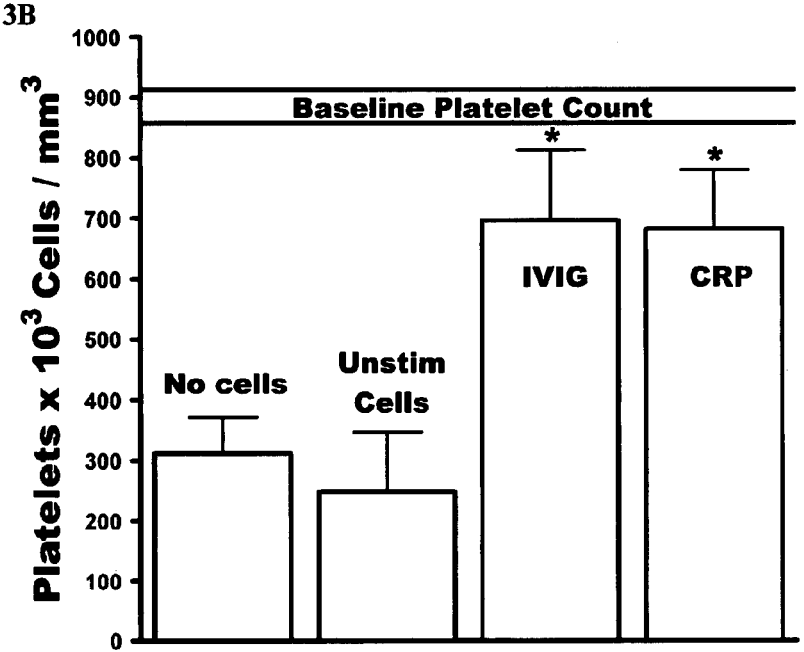

FIGURE 3A, B, C (cont'd)
3C
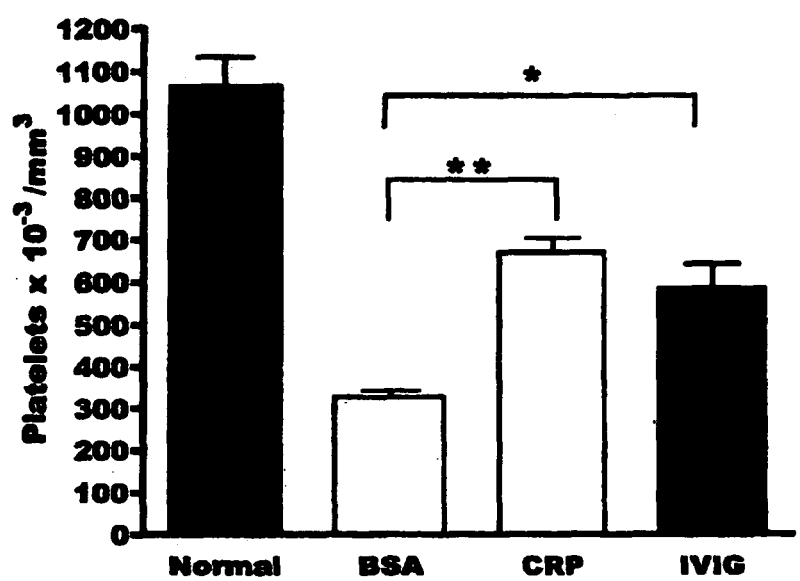

A

B

SEQUENCE LISTING

```
<160> NUMBER OF SEQ ID NOS: 12

<210> SEQ ID NO 1
<211> LENGTH: 206
<212> TYPE: PRT
<213> ORGANISM: Homo sapiens

<400> SEQUENCE: 1

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
```

```
                          165                 170                 175
Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 2
<211> LENGTH: 206
<212> TYPE: PRT
<213> ORGANISM: Homo sapiens

<400> SEQUENCE: 2

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
        50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asn
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 3
<211> LENGTH: 206
<212> TYPE: PRT
<213> ORGANISM: Homo sapiens

<400> SEQUENCE: 3

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
        50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95
```

```
Cys Thr Ser Trp Glu Ser Ala Ser Gly Ile Val Glu Phe Trp Val Ala
            100                 105                 110

Gly Lys Pro Arg Val Arg Lys Ser Leu Lys Lys Gly Tyr Thr Val Gly
            115                 120                 125

Ala Glu Ala Ser Ile Ile Leu Gly Gln Glu Gln Asp Ser Phe Gly Gly
130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
            195                 200                 205

<210> SEQ ID NO 4
<211> LENGTH: 206
<212> TYPE: PRT
<213> ORGANISM: Homo sapiens

<400> SEQUENCE: 4

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu Arg Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
            115                 120                 125

Ala Glu Ala Ser Ile Ile Leu Gly Gln Glu Gln Asp Ser Phe Gly Gly
130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
            195                 200                 205

<210> SEQ ID NO 5
<211> LENGTH: 206
<212> TYPE: PRT
<213> ORGANISM: Homo sapiens

<400> SEQUENCE: 5

Gln Thr Asp Met Ser Arg Lys Ala Phe Val Phe Pro Lys Glu Ser Asp
1               5                   10                  15
```

```
Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
        50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
                100                 105                 110

Gly Lys Pro Arg Val Arg Lys Ser Leu Lys Lys Gly Tyr Thr Val Gly
            115                 120                 125

Ala Glu Ala Ser Ile Ile Leu Gly Gln Glu Gln Asp Ser Phe Gly Gly
            130                 135                 140

Asn Phe Glu Gly Ser Gln Ser Leu Val Gly Asp Ile Gly Asn Val Asn
145                 150                 155                 160

Met Trp Asp Phe Val Leu Ser Pro Ala Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
            195                 200                 205

<210> SEQ ID NO 6
<211> LENGTH: 206
<212> TYPE: PRT
<213> ORGANISM: Homo sapiens

<400> SEQUENCE: 6

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
        50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
                100                 105                 110

Gly Lys Pro Arg Val Arg Lys Ser Leu Lys Lys Gly Tyr Thr Val Gly
            115                 120                 125

Ala Glu Ala Ser Ile Ile Leu Gly Gln Glu Gln Asp Ser Phe Gly Gly
            130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Leu Leu
                165                 170                 175

Gly Gly Pro Phe Ser Pro Asn Val Leu Asn Trp Arg Ala Leu Lys Tyr
            180                 185                 190
```

```
Glu Val Gln Gly Glu Val Phe Thr Lys Pro Gln Leu Trp Pro
        195                 200                 205

<210> SEQ ID NO 7
<211> LENGTH: 206
<212> TYPE: PRT
<213> ORGANISM: Homo sapiens

<400> SEQUENCE: 7

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Gln
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 8
<211> LENGTH: 206
<212> TYPE: PRT
<213> ORGANISM: Homo sapiens

<400> SEQUENCE: 8

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Ala Trp Ser Lys Asp Ile Gly Tyr Ser Phe Thr Val Gly Gly Ser
65                  70                  75                  80

Ala Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
```

```
                  115                 120                 125
Ala Glu Ala Ser Ile Ile Leu Gly Gln Glu Gln Asp Ser Phe Gly Gly
            130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 9
<211> LENGTH: 12
<212> TYPE: PRT
<213> ORGANISM: Homo sapiens

<400> SEQUENCE: 9

Ile Tyr Leu Gly Gly Pro Phe Ser Pro Asn Val Leu
1               5                   10

<210> SEQ ID NO 10
<211> LENGTH: 15
<212> TYPE: PRT
<213> ORGANISM: Homo sapiens

<400> SEQUENCE: 10

Leu Ser Pro Asp Glu Ile Asn Thr Ile Tyr Leu Gly Gly Pro Phe
1               5                   10                  15

<210> SEQ ID NO 11
<211> LENGTH: 20
<212> TYPE: PRT
<213> ORGANISM: Homo sapiens

<400> SEQUENCE: 11

Leu Ser Pro Asp Glu Ile Asn Thr Ile Tyr Leu Gly Gly Pro Phe Ser
1               5                   10                  15

Pro Asn Val Leu
            20

<210> SEQ ID NO 12
<211> LENGTH: 6
<212> TYPE: PRT
<213> ORGANISM: Homo sapiens

<400> SEQUENCE: 12

Lys Pro Gln Leu Trp Pro
1               5
```

SUPPRESSIVE MACROPHAGES, C-REACTIVE PROTEIN AND THE TREATMENT OF SYSTEMIC LUPUS ERYTHEMATOSUS AND IMMUNE THROMBOCYTOPENIC

RELATED APPLICATIONS

This application claims the benefit of priority of provisional application U.S. 60/857,008, filed Nov. 6, 2006, which is incorporated by reference in its entirety herein.

GOVERNMENT RIGHTS STATEMENT

This invention was made with government support under a VA merit review and Grant No. R01 IM028356 awarded by the National Institutes of Health. The government has certain rights in the invention.

FIELD OF THE INVENTION

The present invention relates to the use of C-reactive protein (CRP) in combination with spleen cells and/or peripheral blood cells (monocytes/macrophages and/or dendritic cells) to produce suppressive macrophages and/or dendritic cells for the treatment of systemic lupus erythematosus (SLE) and immune thrombocytopenic purpura (ITP), various disease states, conditions or manifestations associated with SLE, including lupus of the skin (discoid), systemic lupus of the joints, lungs and kidneys, hematological conditions including hemolytic anemia and low lymphocyte counts, lymphadenopathy and CNS effects, including memory loss, seizures and psychosis, among numerous others as otherwise disclosed herein. In another aspect of the invention, the reduction in the likelihood that a patient who is at risk for an outbreak of a disease state or condition associated with SLE will have an outbreak is an additional aspect of the present invention. Further embodiments relate to the use of effective amounts of CRP, its mutants, metabolites and polypeptides and related compounds thereof for the treatment of ITP in patients, alone or optionally in combination with suppressive macrophages and/or dendritic cells, or other agents.

BACKGROUND OF THE INVENTION

C-reactive protein (CRP) is a major acute phase reactant, which is produced primarily in the liver in response to infection, inflammation and trauma (1). CRP has been shown to bind to nuclear autoantigens (2). The primary stimulus for CRP production is IL-6 (3). Serum levels of CRP in disease usually correlate with levels of IL-6 in the blood. In SLE, CRP levels do not correlate with serum IL-6 suggesting an abnormal CRP response in patients with SLE (4).

Extensive efforts to discover the single "function" of CRP have instead demonstrated that CRP exhibits different biological activities under different conditions (1, 3). These activities depend on ligand recognition, activation of complement and interactions with Fc gamma receptors (FcγR) I and II and perhaps FcγRIII. Although CRP may enhance inflammation and ligand clearance through complement activation, one of its most important functions appears to be the direct modulation of inflammation through interaction with FcγR (5). Depending on the level and type of FcγR expressed on cells at the site of CRP interaction, the outcome of CRP binding may be either pro- or anti-inflammatory. Under most conditions it is likely that CRP plays an anti-inflammatory and immunomodulatory role in acute inflammation and helps to clear damaged self and foreign materials from the circulation in a non-inflammatory and non-immunogenic manner.

CRP modulates inflammation in a variety of animal models. Heuertz et al first demonstrated that CRP protects rabbits and mice from C5a induced alveolitis (6, 7). CRP also protects mice from lethality due to lipopolysaccharide (LPS) (8). The ability of CRP to protect mice from LPS was subsequently determined to require FcγR (9). These are acute inflammatory models associated with complement activation and neutrophilic infiltration. However, CRP was also protective in a mouse model of experimental allergic encephalitis (10), a T cell-mediated autoimmune disease.

CRP interacts with nuclear antigens including chromatin and small nuclear ribonuclear protein particles (snRNPs) (reviewed in (2)). In addition, CRP binds to apoptotic cells leading to enhanced phagocytosis and an increase in anti-inflammatory cytokines (11, 12). CRP also influences the course of autoimmune disease in (NZB×NZW)$F_1$ female mice (NZB/W) (13). This effect was attributed to decreased antigenic stimulation and enhanced clearance of nuclear antigens. The protection from nephritis in NZB/W mice was recently confirmed in a transgenic mouse expressing human CRP (14). More recently, the present inventors determined that a single injection of CRP provides long-lasting protection from lupus nephritis and reverses ongoing nephritis in NZB/W mice (15). Interestingly, there was no reduction of autoantibodies to nuclear antigens in CRP-treated mice in either of these studies. CRP was also protective in nephrotoxic nephritis (NTN), an immune complex (IC) nephritis model that does not involve autoantibodies (15). As renal disease was markedly decreased in CRP-treated mice without a corresponding decrease in glomerular IgG or C3 deposition, it appears that CRP can reduce the inflammatory response to IC.

Systemic lupus erythematosus (SLE) is a systemic immune complex disease of humans that affects multiple organ systems. The disease is characterized by rashes, arthritis, lung disease, and kidney disease. It occurs mostly in women and usually strikes during young adulthood. Perhaps the most severely affected organ is the kidney, and glomerulonephritis is the major cause of morbidity and mortality in patients with SLE. The current standard treatment for lupus nephritis is the alkylating agent cyclophosphamide, a strong immunosuppressive drug. Although treatment is generally effective, the drug has many side effects including infections, sterility, hair loss, and malignancy.

A wide variety of agents have been used to treat SLE. These agents may act either by interfering with collaborations between B and T lymphocytes, directly eliminating effector cells, or by blocking individual cytokines. Biological agents have had various levels of success in treating animal models of SLE. However, most agents require repeated treatment with high concentrations of monoclonal antibody or protein antagonists.

The most commonly studied animal model of human SLE is the NZB/W female mouse. This mouse model has many features in common with the human disease including severe proliferative glomerulonephritis, which is the major cause of death in the mice. The mice have high levels of circulating immune complexes (IC), which interact with FcγR in the kidney to induce nephritis. A second mouse model of human SLE is the MRL-Fas$^{lpr}$ mouse (MRL/lpr), which exhibits a more rapid progression of disease than the NZB/W mouse.

The innate immune system plays an important role in autoimmunity. One way in which the innate immune system molecules may affect autoimmunity is through the recognition and clearance of autoantigens released from apoptotic or necrotic cells. Other possible mechanisms for protecting against autoimmune-mediated inflammation include altering the cytokine response to inflammatory stimuli and redirecting the adaptive immune system.

CRP is the prototypic acute phase reactant in man and a component of the innate immune system. CRP binds to nuclear antigens that are the targets of the autoantibodies of patients with SLE as well as to damaged membranes and microbial antigens. CRP activates the classical complement pathway and interacts with phagocytic cells through FcγR. CRP is protective against various inflammatory states including endotoxin shock and inflammatory alveolitis. CRP protection against endotoxin shock requires FcγR and is associated with FcγR-dependent induction of interleukin-10 (IL-10) synthesis by macrophages.

It has been reported that CRP is protective against the accelerated disease in NZB/W mice injected with chromatin. It has also been demonstrated that NZB/W mice transgenic for human CRP had a delayed onset of proteinuria and enhanced survival. The ability of CRP to prolong survival in NZB/W mice has been attributed to increased binding and clearance of autoantigens or immune complexes. However, the ability of CRP to regulate acute inflammation suggests an alternative mechanism for its beneficial effects in SLE.

Immune thrombocytopenic purpura (ITP) is an autoimmune disease characterized by platelet clearance mediated by pathogenic platelet-specific antibodies. Current therapies for ITP include untargeted immunosuppression, splenectomy and high dose intravenous immunoglobulin (IVIG). Approaches that harness the immune system's natural regulatory pathways may be promising alternatives with fewer side effects.

IVIG has been used to treat both ITP and lupus nephritis. Siragam et al. have recently described an adoptive transfer model of IVIG treatment of ITP (3). They had previously shown that IVIG ameliorates thrombocytopenia in this model. They have now determined that spleen cells, and specifically, dendritic cells (DC), treated with IVIG in vitro act through FcγR to transfer suppression to mice treated to induce ITP. Although IVIG is an effective treatment for ITP, and to a lesser degree, SLE, it has several limitations. It must be used in very high doses in vivo and it is expensive. It may occasionally exacerbate disease, either due to aggregates or interaction with FcγRIII.

BRIEF DESCRIPTION OF THE FIGURES

FIG. 1 shows a number of gene sequences for compounds that are used in the present invention.

FIGS. 3A, B and C show the design and results of an adoptive transfer model for CRP and IVIG-mediated suppression of ITP. Spleen cells were treated in vitro with CRP (200 μg/ml) or intravenous immunoglobulin (IVIG) (18 mg/ml) for 30 min at 37° C. in RPMI medium without serum. Untreated (3B) or bovine serum albumin (BSA)-treated (3C) spleen cells were used as controls, equivalent to no cell transfer. Cells were washed once with RPMI and $10^6$ cells/mouse were injected i.v. into recipient mice. Recipients were treated 24 h later with 5 μg of anti-CD41 (anti-platelet antibody) i.v. Blood samples were taken and platelets were counted before injection (normal) and 24 h later. Results are mean±SEM, n=3, *p<0.05, **p<0.01.

FIG. 8A shows macrophages expressing FcγRI (from FcgRIIb$^{-/-}$ mice). FIG. 8B shows macrophages expressing FcγgRIIb (from FcR g-chain$^{-/-}$ mice). The results show that CRP mutant Y175L has increased binding to FcγRI on mouse macrophages and normal binding to FcγRIIb.

BRIEF DESCRIPTION OF THE INVENTION

Figure 2:
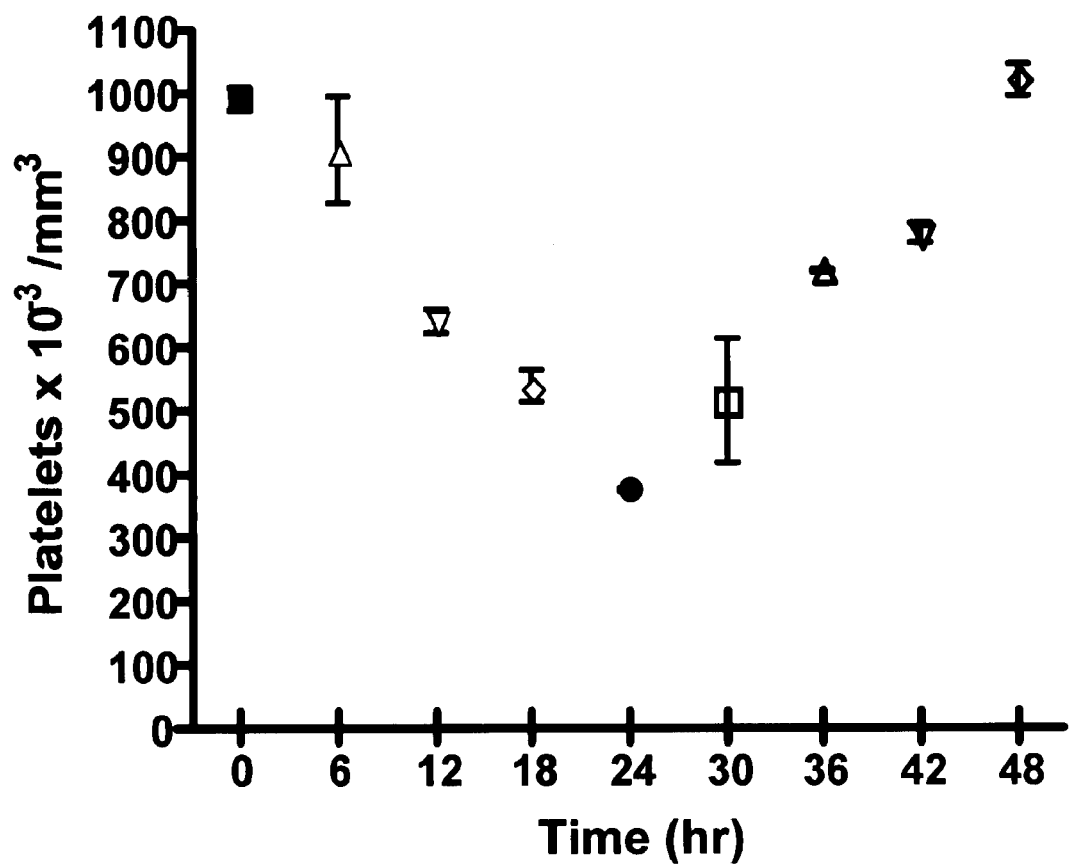
FIG. 2 shows the experimental model of ITP that was used to test CRP-mediated suppression. Platelet counts indicate the time course of thrombocytopenia following injection of 5 μg anti-CD41, anti-platelet antibody at 0 h.

The present invention relates to the use of C-reactive protein (CRP) or its mutants, metabolites, polypeptides and related compounds such as multimers as otherwise described herein ("CRP-related compounds") to create CRP-activated monocyte cells (suppressive macrophages or dendritic cells) which may be used alone or in combination with other agents to treat systemic lupus erythematosus and/or immune thrombocytopenic purpura (ITP) in a patient, especially a human patient. In this method, spleen cells, bone marrow-derived macrophages, or peripheral blood cells (preferably autologous cells from the patient) are first activated with cytokines to produce non-activated macrophages which are then exposed to effective concentrations of C-reactive protein or its related compounds and then administered to a patient with SLE or ITP, alone or in combination with additional CRP in order to treat same.

In alternative embodiments of the present invention, CRP or its mutants, metabolites and polypeptides and related compounds thereof may be administered directly (i.e., in the absence of suppressive macrophages) to the patient to treat ITP, ameliorate the conditions, symptoms or disease states associated with ITP or reduce the likelihood that the conditions, symptoms or disease states associated with ITP will worsen in a patient.

The present method can be used to treat ITP as well a number of disease states or conditions that occur secondary to ITP or to systemic lupus erythematosus (SLE). The present invention relates to the use of CRP or CRP-related compounds to expose monocytes and produce suppressive macrophages and/or dendritic cells, which may be used to treat SLE and/or ITP. In particular aspects of the invention, any one or more of secondary conditions, disease states or manifestations of SLE include serositis, malar rash (rash over the cheeks and bridge of the nose), discoid rash (scaly, disk-shaped sores on the face, neck and chest), sores or ulcers (on the tongue, in the mouth or nose), arthritis, hemolytic anemia, lymphadenopathy, low lymphocytic count, low platelet count, the presence of antinuclear antibodies in the blood, skin lesions, CNS effects (including loss of memory, seizures, strokes and psychosis), lung symptoms/effects including inflammation (pleuritis), chronic pneumonitis, chronic diffuse interstitial lung disease and scarring of the lungs, hair loss, Raynaud's syndrome, lupus nephritis, sensitivity to light, fatigue, fever, nausea, vomiting, diarrhea, swollen glands, lack of appetite, sensitivity to cold (Raynaud's phenomenon) and weight loss is treated using the suppressive macrophages and pharmaceutical compositions based upon same according to the present invention.

In the case of ITP, reduction in the symptoms of bleeding, red dots on the skin, red dots on the mouth membranes, purplish mouth membrane areas, bleeding nose, bleeding gum, digestive bleeding, urinary bleeding and brain bleeding are measures of success. In the case of ITP, there is an increased platelet count pursuant to successful therapy.

In one aspect, the method of the present invention comprises removing peripheral blood cells, spleen cells or bone marrow cells from a patient or subject, exposing monocytes obtained therefrom (with or without further separation) to a growth/differentiation factor (such as a cytokine (γ-IFN) for macrophages or granulocyte monocyte colony stimulating factor (GM-CSF) and interleukin-4 (IL-4) for dendritic cells) to produce macrophages and/or dendritic cells. These macrophages and/or dendritic cells are then exposed to an effective amount of CRP or a CRP-related compound as otherwise described herein to produce suppressive macrophages and/or dendritic cells. These suppressive cells, in whole blood, a monocyte fraction of cells or as purified/isolated cells, are administered to a patient in effective amounts either alone or optionally, in combination with CRP, a CRP-related compound and/or another agent as disclosed herein to a patient suffering from SLE or ITP.

The suppressive macrophage and/or dendritic cells used in the present invention are preferably autologous to the patient or subject and are preferably administered in the presence of a pharmaceutically acceptable additive, carrier or excipient.

In certain aspects of the invention, monocytes obtained from peripheral blood (buffy coat), spleen or bone marrow of a subject or patient may be exposed directly to an effective amount of CRP to produce suppressive macrophages and/or dendritic cells without first being exposed to a growth/differentiation factor as described hereinabove. The resulting suppressive cells may be used with or without further purification in effective amounts to treat a patient suffering from SLE or ITP, optionally in combination with at least one additional agent selected from CRP, a CRP-related compound or another agent as disclosed herein.

In further embodiments, the present invention relates to a population of isolated monocyte cells exposed to an amount of CRP or a CRP-related compound effective to produce suppressive macrophages and/or dendritic cells. The monocyte cells may be obtained from a peripheral blood sample of a subject (in whole blood or preferably, in the buffy coat), or from the spleen or bone marrow of a patient or subject. Prior to exposure to CRP or a CRP-related compound, the monocyte cells may be first exposed to a growth/differentiation factor (such as a cytokine (γ-IFN) for macrophages or granulocyte monocyte colony stimulating factor (GM-CSF) and interleukin-4 (IL-4) for dendritic cells) to produce macrophages and/or dendritic cells.

The suppressive macrophages of the present invention express CD11b and are characterized by at least one of the following: secretion of interleukin 10 or decreased phagocytosis of rabbit anti-erythrocyte antibody coated sheepβ erythrocytes.

Pharmaceutical compositions comprising an effective amount of suppressive macrophages and/or dendritic cells as otherwise described herein, optionally in the presence of CRP, a CRP-related compound and/or another agent useful for treating SLE or ITP and optionally, a pharmaceutically acceptable additive, carrier or excipient are additional aspects of the present invention.

In alternative embodiments of the invention, a compound according to the present invention (suppressive macrophage and/or dendritic cells or CRP, or a CRP-related compound, which are active against SLE or ITP alone or in combination with an active carrier) may be coadministered with an effective amount of at least one additional agent which is traditionally used in the treatment of system lupus erythematosus or immune thrombocytopenic purpura (ITP). These agents may include, for example, non-steroidal anti-inflammatory drugs (NSAIDs) including traditional NSAIDs, COX-2 inhibitors and salicylates (such as aspirin), anti-malarials such as hydroxychloroquine, quinacrine, corticosteroids such as prednisone (Deltasone), betamethasone (Celestone), methylprednisolone acetate (Medrol, Depo-Medrol), hydrocortisone (Cortef, Hydrocortone) and dexamethasone (Decadron, Hexadrol), among others and immunosuppressants such as methotrexate (Rheumatrex), cyclophosphamide (Cytoxan), Azathioprine (Imuran) and mycophenolate (mofetil, MMF, also CellCept). In the case of ITP, the treatment may include a corticosteroid (as described above) or an immunosuppressant. In one embodiment, agents to be used for ITP treatment include dexamethasone or prednisone.

The present invention also relates to a method of suppressing autoantibody production in a patient comprising administering to said patient an effective amount of suppressive macrophages alone or in combination with an effective amount of C-reactive protein (CRP), in combination with a pharmaceutically acceptable additive, excipient, or carrier.

DETAILED DESCRIPTION OF THE INVENTION

The following terms shall be used to describe the present invention.

The term "patient" or "subject" refers to an animal, such as a mammal, including a human, in need of treatment or therapy to which compounds according to the present invention are administered in order to treat a condition or disease state associated with systemic lupus erythematosus treatable or ITP using compounds or compositions according to the present invention. The term patient also refers to domesticated animals, such as dogs, cats, pigs, horses, cows, sheep, etc. The term also refers to an animal from which a sample of peripheral blood, monocytes, macrophages or dendritic cells are obtained and isolated.

The term "compound" is used herein to refer to any specific chemical compound disclosed herein. Within its use in context, the term generally refers to a single compound, such as a polypeptide or a related polymeric compound (generally containing repeating units and a molecular weight) or a small molecule bioactive agent (typically, a compound which is not polymeric, which may be natural or synthetic, having a molecular weight of about 2,500 or less or 2,000 or less).

The term "isolated" shall mean purified from a natural source such that a desired cell such as a monocyte, macrophage or dendritic cell is obtained at a higher concentration than the sample from which the isolated cells are obtained. Isolation of cells may occur using one or more methods, which are well known in the art including centrifugation techniques or other cell separation techniques including using magnetic separation or fluorescent activated cell sorting, techniques, which are known in the art.

The term "systemic lupus erythematosus", "SLE" or "lupus" is used to describe a chronic potentially debilitating or fatal autoimmune disease in which the immune system attacks the body's cells and tissue, resulting in inflammation and tissue damage. SLE refers to several forms of an immunologic disease that affects the joints, skin, muscles, face and mouth, kidneys, central nervous system and other parts of the body. SLE is a chronic and inflammatory disease that can potentially be fatal. SLE can either be classified as an autoimmune or a rheumatic disease. Changes in symptoms are called flares and remissions. Flares are periods when SLE becomes more active with increased symptoms, and remissions are periods when few or no symptoms of lupus are present. In the United States alone, an estimated 270,000 to 1.5 million or more people have SLE, with an estimated 5 million worldwide, having the disease. It is more common than cystic fibrosis or cerebral palsy.

The specific cause of SLE is unknown. It is considered to be a multifactorial condition with both genetic and environmental factors involved. In a multifactorial condition, a combination of genes from both parents, in addition to unknown environmental factors, produce the trait, condition, or disease. It is known that a group of genes on chromosome 6 that code for the human leukocyte antigens play a major role in a person's susceptibility or resistance to the disease. The specific HLA antigens associated with SLE are DR2 and DR3. When the immune system does not function properly, it loses its ability to distinguish between its own body cells and foreign cells. Antinuclear antibodies are autoantibodies (antibodies that fight the body's own cells) that are produced in people with SLE. They often appear in the blood of a patient with SLE.

Studies suggest that some people may inherit the tendency to get SLE, and new research suggests that new cases of SLE appear to be more common in families in which one member already has the disease. However, there is no evidence that supports that SLE is directly passed from parent to child. Females in their childbearing years (18-45) are eight to ten times more likely to acquire SLE than men, and children and the elderly can also acquire the disease.

SLE is unpredictable, and no two people have exactly the same manifestations of the disease. There are 11 criteria that help doctors tell the difference between people who have SLE and people who have other connective tissue diseases. If a person displays 4 or more of the following 11 criteria, the person fulfills the requirement for the diagnosis of SLE.

1. Malar rash—a butterfly shaped rash over the cheeks and across the bridge of the nose;
2. Discoid rash—scaly, disk-shaped sores on the face, neck, and chest;
3. Serositis—inflammation of the lining around the heart, lungs, abdomen, causing pain and shortness of breath;
4. Photosensitivity—skin rash as an unusual reaction to sunlight;
5. Sores or ulcers on the tongue, mouth, or in the nose;
6. Arthritis;
7. Kidney disorder—persistent protein or cellular casts in the urine;
8. Central nervous system problems including seizures and psychosis;
9. Blood problems such as low white blood cell count, low lymphocyte count, low platelet count, or hemolytic anemia;
10. Immune system problems (immune dysfunction/dysregulation)—presence of abnormal autoantibodies to double stranded DNA, Sm antigen or phospholipid in the blood; and
11. Presence of abnormal antinuclear antibodies in the blood.

Other symptoms/manifestations of SLE include inflammatory lung problems, lymphadenopathy, fever, nausea, vomiting, diarrhea, swollen glands, lack of appetite, sensitivity to cold (Raynaud's phenomenon), weight loss, and hair loss.

Notwithstanding the numerous disease states, conditions and/or manifestations associated with SLE, it is difficult to diagnose because there is no single set of signs and symptoms to determine if a person has the disease. There is no single test that can diagnose SLE. Some tests used to diagnose SLE include urinalysis to detect kidney problems, tests to measure the amount of complement proteins in the blood, complete blood cell counts to detect hematological disorders, and an ANA test to detect antinuclear antibodies in the blood. Additionally, X-rays may be ordered to check for lung and heart problems.

The term "immune thrombocytopenic purpura" or "ITP" is used throughout the specification to describe an autoimmune disease characterized by platelet clearance mediated by pathogenic platelet-specific antibodies. The disease is characterized by reduced blood platelets, which cause visible skin blemishes from bleeding or bruising. Symptoms can include the following: bleeding, red dots on the skin, red dots on the mouth membranes, purplish mouth membrane areas, bleeding nose, bleeding gum, digestive bleeding, urinary bleeding and brain bleeding. Immune thrombocytopenic purpura (ITP) is a clinical syndrome in which a decreased number of circulating platelets (thrombocytopenia) manifests as a bleeding tendency, easy bruising (purpura), or extravasation of blood from capillaries into skin and mucous membranes (petechiae).

In persons with ITP, platelets are coated with autoantibodies to platelet membrane antigens, resulting in splenic sequestration and phagocytosis by mononuclear macrophages. The resulting shortened life span of platelets in the circulation, together with incomplete compensation by increased platelet production by bone marrow megakaryocytes, results in a decreased platelet count.

To establish a diagnosis of ITP, other causes of thrombocytopenia are excluded, such as leukemia, myelophthisic marrow infiltration, myelodysplasia, aplastic anemia, or adverse drug reactions. Pseudothrombocytopenia due to platelet clumping is also a diagnostic consideration. No single laboratory result or clinical finding establishes a diagnosis of ITP; it is a diagnosis of exclusion.

Pathophysiology: An abnormal autoantibody, usually immunoglobulin G (IgG) with specificity for 1 or more platelet membrane glycoproteins (GPs), binds to circulating platelet membranes. Autoantibody-coated platelets induce Fc receptor-mediated phagocytosis by macrophages, primarily but not exclusively in the spleen. The spleen is the key organ in the pathophysiology of ITP not only because platelet autoantibodies are formed in the white pulp but also because macrophages in the red pulp destroy immunoglobulin-coated platelets.

If bone marrow megakaryocytes cannot increase production and maintain a normal number of circulating platelets, thrombocytopenia and purpura develop. Impaired thrombopoiesis is attributed to failure of a compensatory increase in thrombopoietin and megakaryocyte apoptosis.

In the U.S., the annual incidence of chronic ITP is estimated to be 5.8-6.6 cases per 100,000 persons, but these data are not from large population-based studies. Most cases of acute ITP, particularly in children, are mild and self-limited and may not receive medical attention. Therefore, estimated incidences of acute ITP are difficult to determine and likely to understate the full extent of the disease.

The primary cause of long-term morbidity and mortality is hemorrhage. The most frequent cause of death in association with ITP is spontaneous or accidental trauma-induced intracranial bleeding in patients whose platelet counts are less than $10\times10^9$/L (<$10\times10^3$/mL). This situation occurs in less than 1% of patients.

To maintain a platelet count in a safe range in patients with chronic treatment-resistant ITP, a long-term course of corticosteroids, other immunosuppressive medications, or splenectomy may be required. In patients with this disease, morbidity and mortality can be related to treatment, reflecting the complications of therapy with corticosteroids or splenectomy.

In children, the prevalence is the same among boys and girls. In adults, women are affected approximately 3 times more frequently than men. Children may be affected at any age, but the prevalence peaks in children aged 3-5 years. Adults may be affected at any age, but most cases are diagnosed in women aged 30-40 years. Onset in a patient older than 60 years is uncommon, and a search for other causes of thrombocytopenia is warranted. The most likely causes in these persons are myelodysplastic syndromes, acute leukemia, and marrow infiltration (myelophthisis).

The term "effective" shall mean, within context, a number of cells, an amount of a compound, composition or component, for a duration of time (which may be at a given time and/or vary considerably depending upon the disease state, condition or manifestation to be treated or to have a reduced likelihood of occurring) which produces an intended effect. In instances where suppressive macrophages are administered (coadministration) along with CRP, a CRP-related compound and/or another agent (such as a corticosteroid or immunosuppressive agent, among others) is used for the treatment of ITP in patients, the number of cells or the amount of compound or component that is used is an effective amount to produce a desired or intended effect, very often, a favorable therapeutic outcome.

The term "treatment" or "treating" is used to describe an approach for obtaining beneficial or desired results including and preferably clinical results. For purposes of this invention, beneficial or desired clinical results include, but are not limited to, one or more of the following: alleviation of one or more symptoms, diminishment of extent of disease, stabilized (i.e., not worsening) state of disease, preventing or reducing the likelihood of the spread of disease, reducing the likelihood of occurrence or recurrence of disease, decreasing, delaying or reducing the likelihood of the occurrence of "flares," amelioration of the disease state, remission (whether partial or total), reduction of incidence of disease and/or symptoms, stabilizing (i.e., not worsening) of immune or renal function or improvement of immune or renal function. "Flares" refer to an increase in activity, generally inflammatory activity in a particular tissue. The "treatment" of SLE may be administered when no symptoms of SLE are present, and such treatment (as the definition of "treatment" indicates) reduces the incidence or likelihood of flares. Also encompassed by "treatment" is a reduction of pathological consequences of any aspect of SLE, ITP or any associated disease states or conditions, including skin rashes (malar and discoid), arthritis, serositis (inflammation of the lining around the heart, lungs, abdomen), sores (mouth, nose and tongue), immune dysfunction/dysregulation, central nervous system problems (including psychosis, seizures and strokes), blood problems (including low white blood cell count, low platelet count, or anemia), the presence of antinuclear antibodies in the blood and kidney disease/dysfunction (especially SLE-related nephritis) and any of the related conditions, disease states or symptoms of ITP as otherwise described hereinabove. In the case of ITP, favorable treatment generally will result in an increased platelet count. Also, in the case of ITP, one or more of the symptoms/conditions of ITP including bleeding, red dots on the skin, red dots on the mouth membranes, purplish mouth membrane areas, bleeding nose, bleeding gum, digestive bleeding, urinary bleeding and brain bleeding associated with ITP are reduced and/or eliminated with successful therapy.

"SLE flares" are used herein to refer to flares (i.e. acute clinical events) which occur in patients with SLE. The SLE flares may be in various major organs, including but not limited to, kidney, brain, lung, heart, liver, connective tissues and skin. Flares can include activity in all tissues that may be affected by SLE. Remission is a term used to refer to periods of little or no lupus symptoms.

"Reducing incidence" of renal flares in an individual with SLE means any of reducing severity (which can include reducing need for and/or amount of (e.g., exposure to) other drugs generally used for this conditions, including, for example, high dose corticosteroid and/or cyclophosphamide), duration, and/or frequency (including, for example, delaying or increasing time to renal flare as compared to not receiving treatment) of renal flare(s) in an individual.

The term "C-reactive protein" or "CRP" is used herein to describe a 206 amino acid protein, which is a member of the class of acute phase reactants as its levels rise dramatically during inflammatory processes occurring in the body. It is thought to assist in removal of damaged cells and affect the humoral response to disease. It is also believed to play an important role in innate immunity, as an early defense system against infections. CRP is used mainly as a marker of inflammation. CRP is the prototypic acute phase reactant in humans and is a component of the innate immune system. CRP binds to nuclear antigens that are the target of the autoantibodies of patients with SLE as well as to damaged membranes and microbial antigens. CRP activates the classical complement pathway and interacts with phagocytic cells through FcγR. CRP is protective against various inflammatory states including endotoxin shock and inflammatory alveolitis. CRP protection against endotoxin shock requires FcγR and is associated with FcγR-dependent induction of interleukin-10 (IL-10) synthesis by macrophages.

CRP is an acute phase serum protein that provides innate immune recognition, opsonization, and regulation of autoimmunity and inflammation. CRP may bind several autoantigens in SLE, for example SmD1 and 70K proteins of Sm and RNP, histones, and chromatin. CRP may activate complement and may bind to FcγRI and FcγRII in man and mouse. CRP is a natural product found in the serum of people, and it is believed to be nontoxic.

CRP has 206 amino acid units. The entire sequence of C-reactive protein appears in FIG. 1 (SEQ ID NO:1). The polypeptide sequence of CRP also has the following Accession numbers: BC125135, NM_000567, BC070257, BC020766, M11880, M11725, X56214 and X56692, all of which sequences are incorporated by reference herein. SEQ ID NO:1 (FIG. 1) is also represented as follows:

(SEQ ID NO: 1)
QTDMSRKAFVFPKESDTSYVSLKAPLTKPLKAFTVCLHFYTELSSTRGY

SIFSYATKRQDNEILIFWSKDIGYSFTVGGSEILFEVPEVTVAPVHICT

SWESASGIVEFWVDGKPRVRKSLKKGYTVGAEASIILGQEQDSFGGNFE

GSQSLVGDIGNVNMWDFVLSPDEINTIYLGGPFSPNVLNWRALKYEVQG

EVFTKPQLWP

In one aspect of the invention, C-reactive protein is prepared as a dosage formulation for delivery to a human patient and administered in order to produce suppressive macrophage or dendritic cells to treat SLE or ITP or any one or more of the secondary disease states, conditions or symptoms which occur in a patient with ITP. Alternatively CRP may be used directly (i.e. in the absence of or optionally, the presence of suppressive macrophages or dendritic cells) in effective amounts to treat ITP or any one of the secondary disease states, conditions or symptoms that occur in a patient with ITP.

Human CRP may be purified from human pleural effusion fluid. T. W. Du Clos, "C-reactive protein reacts with the U1 small nuclear ribonucleoprotein," *J. Immunol.* 143:2553-2559 (1989). For example, human pleural fluids may be obtained from discarded drains of patients undergoing surgery. The fluids may be clarified by high speed centrifugation. The CRP may be partially purified by affinity chromatography on phosphocholine (PC)-Sepharose and then may be further purified by gel filtration chromatography. The CRP may then be further purified by affinity chromatography on PC-Sepharose. For final purification, the protein may be purified by mono Q based FPLC. A major band should be seen at about 25 kDa on SDS-PAGE. The final preparation may then be filter-sterilized and endotoxin contamination may be measured by a limulus-based assay from Cambrex (East Rutherford, N.J.). Endotoxin may be removed using Acticlean Etox (Sterogene Bioseparations Inc., Carlsbad, Calif.) to reduce preparations to less than 0.3 ng of endotoxin/mg of protein.

Alternatively, CRP may be produced as a recombinant protein following general procedures well known in the art. U.S. Pat. No. 5,702,921 to Tanaka describes the production of human C-reactive protein using *Escherichia coli* vectors described therein. Recombinant CRP may also be produced using a baculovirus expression system as described in Marnell et al. *Protein Expression and Purification* 6:439, 1995.

Other polypeptides useful in the present invention may be readily synthesized using well-known genetic engineering techniques or polypeptide synthetic methods, especially for the polypeptides, multimers based upon same or compounds comprising a polypeptide that is complexed to a carrier for therapeutic delivery. Polypeptides according to the present invention may be useful as therapies for direct treatment (i.e., without concomitant administration of suppressive macrophages as otherwise described herein) of ITP and in particular, one or more of the disease states, conditions or symptoms associated with ITP, as standards or as research tools for assisting in further research to determine the structure of optimal polypeptides useful in treating ITP, or to provide three dimensional structural features for developing small molecule mimetics and agents useful in treating ITP or any one or more of the disease states, conditions or symptoms associated with ITP.

The term "mutant", "C-reactive protein mutant" or "CRP mutant" is used to describe a mutant C-reactive protein according to the present invention where the naturally occurring sequence of CRP (SEQ ID NO: 1) has been altered at one or more amino acids in the naturally occurring sequence. Mutants for use in the present invention have altered amino acids (non-naturally occurring amino acids) at amino acid residue 112 of the naturally occurring (wild-type) C-reactive protein (Asn, Gln, Arg, Ala, Leu, Ile or Val for the naturally occurring asp), at amino acid residue 38 (Arg, Asn or Gln for naturally occurring His), at amino acid residue 169 (Ala, Leu, Ile or Val for the naturally occurring Asp), at amino acid 175 (Ala, Leu, Ile or Val for the naturally occurring Tyr), at amino acid 176 (Gln, Asn, Arg, Ala, Ile or Val for the naturally occurring Leu) and in a double mutant at amino acids 66 and 81, at amino acid residue 66 (Ala, Leu, Ile or Val for the naturally occurring Phe at 66) and at amino acid residue 81 (Ala, Leu, Ile or Val for the naturally occurring Glu at 81). Preferred mutant polypeptides for use in the present invention include D112N (Asn substituted for Asp at amino acid 112), D112A (Ala substituted for Asp at amino acid 112), H38R (Arg substituted for His at amino acid 38), D169A (Ala substituted for Asp at amino acid 169), Y175L (Leu substituted for Tyr at amino acid 175), L176Q (Gln substituted for Leu at amino acid residue 176) and the double mutant F66A/E81A (Ala substituted for Phe at amino acid residue 66 and Ala substituted for Glu at amino acid residue 81). The amino acid sequences of the naturally occurring C-reactive protein (SEQ ID. NO:1), and mutants D112N (SEQ ID NO:2), D112A (SEQ ID NO: 3), H38R (SEQ ID NO:4), D169A (SEQ ID NO:5), Y175L (SEQ ID NO:6), L176Q (SEQ ID NO:7) and the double mutant F66A/E81A (SEQ ID NO:8) are presented in attached FIG. 1. All of these polypeptides are useful alone or in combination for the production of suppressive macrophages and/or dendritic cells, or in the treatment of ITP or one or more of its associated symptoms, conditions or disease states as otherwise described herein.

The term "active carrier" shall be used in context to describe a complex molecule, including a polymer which can be used in combination with a C-reactive protein polypeptide, smaller chain polypeptides such as the 6-15 amino acid polypeptides of C-reactive protein as otherwise disclosed here) or multimers according to the present to facilitate delivery of a polypeptide. An active carrier may be an oligomeric polypeptide, such as oligo- or polylysine, oligo- or polyarginine, or a mixture thereof (generally from about 5-1000 mer or greater, but also ranging from about 10 to about 100 mer), polyglutamic acid, polyaspartic acid, polyhistidine, polyasparagine, polyglutamine, etc. or a dendrimer as otherwise disclosed in US patent publication 2003/0232968 to Chun Li, et al. Additional dendrimers are available from Sigma-Aldrich, USA or Dendritic Nano Technologies, Inc., Mount Please, Mich., USA. Dendrimers may include PAMAM dendrimers, phosphorous dendrimers, polypropylenimine dendrimers, and lysine dendrimers, among numerous others. Also called a cascade molecule, a dendrimer is a polymer that has many branches that move out from a core, generally a carbon core. Many of these dendrimers are available commercially from Sigma-Aldrich or from Dendritic Nano Technologies. The term "active carrier" is distinguishable from a conventional pharmaceutical carrier (such as saline solution, etc.) which is also contemplated to be used in certain aspects of the present invention.

Other ways of attaching the protein or polypeptide include modification of a particle surface by adsorption or covalent attachment of suitable linking group(s) to which the protein may be subsequently attached. Examples of additional carriers include polyethylene glycol (with an average molecular weight ranging from about 100 to about 2000), polyethylene glycol co-polypropylene glycol copolymer (random or block copolymers) of similar molecular weight as the polyethylene glycol, albumin (preferably human serum albumin for human therapies), collagen (preferably human recombinant collagen), gelatin, dextran (including cyclodextrin), alginate, polylactide/glycolide, polyhydroxy-butyrate, polyvinyl alcohol, polyanhydride microspheres and liposomes, among others. One of ordinary skill will readily recognize how to complex or attach the present therapeutic polypeptides to active carriers using techniques and methodologies which are well known in the art.

The term "short-chain polypeptide" refers to a polypeptide having a length of at least 6 amino acid units, preferably at least about 10 amino acid units that are useful in the present invention.

Certain short-chain polypeptides are preferred for use in the present invention. Other short-chain polypeptides are also useful in the present invention. Their sequences are:

```
                                             (SEQ ID NO: 9)
Ile Tyr Leu Gly Gly Pro Phe Ser Pro Asn Val Leu
(IYLGGPFSPNVL)
Corresponding to amino acid units 174-185 of CRP;

(SEQ ID NO: 10)
Leu Ser Pro Asp Glu Ile Asn Thr Ile Tyr Leu Gly
Gly Pro Phe (LSPDEINTIYLGGPF)
Corresponding to amino acid units 166-180 of CRP;

(SEQ ID NO: 11)
Leu Ser Pro Asp Glu Ile Asn Thr Ile Tyr Leu Gly
Gly Pro Phe Ser Pro Asn Val Leu
(LSPDEINTIYLGGPFSPNVL)
Corresponding to amino acid units 166-185 of CRP;
At least 10 to 19 (10, 11, 12, 13, 14, 15, 16,
17, 18 or 19) contiguous amino acids of the
polypeptide sequence of SEQ ID NO: 11);

(SEQ ID. NO: 12)
Lys Pro Gln Leu Trp Pro (KPQLWP)
Corresponding to amino acid units 201-206 of CRP.
```

The polypeptides of the present invention may be administered directly as a pharmaceutical composition when combined with a pharmaceutically acceptable additive, carrier or excipient or alternatively, may be used in combination with a carrier (adsorbed or covalently bound to the carrier as otherwise described herein) or to form multimers comprising the polypeptides. These are useful in the treatment of ITP as otherwise described herein.

The term "multimer" is used to describe peptide compounds according to the present invention which are used as multiples of the individual polypeptide units found in the simplest peptide compounds according to the present invention (which range from 6 amino acid units to 20 amino acid units or more). For example, a dimer may be a multiple of a 6 amino acid unit polypeptide (i.e., 12 amino acid units), a multiple of a 10 amino acid unit polypeptide (i.e., 20 amino acid units), an 11 amino acid unit polypeptide (i.e., 22 amino acid units), etc., whereas a trimer is a peptide of a triple multiple of a basic polypeptide. Thus, the term multimer refers to a polypeptide that is incorporated in a molecule in repeating units or chains. Multimers include dimers, trimers, tetramers, pentamers, hexamers, heptamers, octamers, etc. up to as many as 50 or 100 repeat units or more. In certain embodiments, a multimer contains between 2 and 6 repeat units (dimers, trimers, tetramers, pentamers and hexamers).

The individual units of multimers according to the present invention may be linked in a variety of ways including the use of disulfide bonds between cysteinyl residues at the amino or carboxyl end of the polypeptide unit, or alternatively, through peptide bonds (amide linkages) or other chemical linkers at the amino or carboxy terminus of the individual polypeptide units. Multimers according to the present invention are usually no more than dodecamers (12 individual polypeptide units), and in certain embodiments are dimers, trimers or tetramers, or in other embodiments, dimers.

The term "CRP-related compound" refers collectively, to CRP mutants, metabolites, polypeptides and related compounds such as multimers that may be used in the present invention.

The term "coadministration" or "combination therapy" is used to describe a therapy in which at least two active compounds in effective amounts are used to treat systemic lupus erythematosus or ITP, or a related disease state, condition or manifestation at the same time. Although the term coadministration preferably includes the administration of two active compounds to the patient at the same time, it is not necessary that the compounds be administered to the patient at the same time, although effective amounts of the individual compounds will be present in the patient at the same time.

"Naturally occurring" refers to an endogenous chemical moiety, such as a polypeptide or polynucleotide sequence or a carbohydrate, i.e., one found in nature. Processing of naturally occurring moieties can occur in one or more steps, and these terms encompass all stages of processing. Conversely, a "non-naturally occurring" or "synthetic" moiety refers to all other moieties, i.e., ones that do not occur in nature, such as recombinant polynucleotide sequences and non-naturally occurring carbohydrates.

In one aspect of the invention, C-reactive protein or a CRP-related compound in effective amounts is used to prepare suppressive macrophages and/or dendritic cells which may be administered alone or in combination with CRP and/or a CRP-related compound or an other agent as otherwise described herein as a dosage formulation for delivery to a patient, especially a human patient in order to treat systemic lupus erythematosus (SLE), ITP or any one or more of the secondary disease states, conditions or symptoms which occur in a patient with SLE or ITP. In this aspect of the invention, For example, immature (monocyte/macrophage) cells which express the cell surface marker CD11b at high levels and CD11c+ at low levels (e.g., about $1\times10^4$ to about $1\times10^8$ or more cells) are exposed to effective concentrations of CRP or a CRP-related compound in an effective amount (in the case of CRP, at about 10 µg per ml to about to 1 mg per ml or higher, about 100 µg per ml to about 500 µg per ml, at about 100 µg per ml to about 300 µg per ml, including about 200 µg per ml and in the case of a CRP-related compound in amounts which may vary outside of the range for CRP) in cell growth medium as otherwise described herein for a period (about 15 minutes to an hour or more up to a day, about 30 minutes) sufficient to activate the macrophage cells to produce suppressive macrophages and/or dendritic cells prior to administration. One of ordinary skill will know how to readily adjust the conditions associated with the present invention to maximize favorable therapeutic results accordingly.

Alternatively, monocytes isolated from peripheral blood may in some cases be treated for 24-72 hours with 400 U/ml gamma interferon to induce maturation, which is characterized by upregulation of CD64 (FcγRI) and HLA class II molecules prior to exposure to effective amounts of CRP or a CRP-related compound. Purified monocytes also may be differentiated in vitro into macrophages or dendritic cells by 5-8 days of culture in differentiation medium (as otherwise described herein) containing 2% autologous plasma (for suppressive macrophages) or granulocyte monocyte colony stimulating factor (GM-CSF) and interleukin-4 (IL-4) (for dendritic cells). After activation to the suppressive phenotype by CRP treatment the cells would be washed with physiological buffered saline prior to injection into a patient (in a carrier such as isotonic or buffered saline solution). The actual number of cells transferred into the patient would range from about $10^4$ to about $10^8$, about $10^5$ to about $10^8$.

Although advantageous, separation of the monocyte population from the peripheral blood mononuclear cell population is not required. Thus, one could obtain the buffy coat (monocyte cell population) from the patient's blood and treat these cells before or after separation. The presence of other cells within the monocyte cell population does not reduce the effectiveness and may in some instances, enhance the effectiveness of the treatment.

The active cell type (suppressive macrophages or dendritic cells) that has been identified to date in the mouse model is a macrophage expressing FcγRI. In human peripheral blood, monocytes are the primary FcγRI-expressing cell. Monocytes are isolated from human peripheral blood mononuclear cells (from the patient to be treated) by positive selection for CD14, a human monocyte marker. Peripheral blood mononuclear cells or purified monocytes may be treated with an effective amount of CRP as otherwise described herein, in certain preferred aspects, about 100-200 μg/ml of CRP. Generation of suppressive macrophage or dendritic cells by CRP treatment are indicated functionally by secretion of IL-10 and/or decreased phagocytosis of antibody-coated erythrocytes.

In certain embodiments of the invention, monocytes isolated from peripheral blood may in some cases be treated for 24-72 hours with 400 U/ml gamma interferon in differentiation medium to induce maturation, which is characterized by upregulation of CD64 (FcγRI) and HLA class II molecules. Alternatively, purified monocytes may be differentiated in vitro into macrophages or into dendritic cells by 5-8 days of culture in differentiation medium (as otherwise described herein) containing 2% autologous plasma (for macrophages) or granulocyte monocyte colony stimulating factor (GM-CSF) and interleukin-4 (IL-4) (for dendritic cells). Following activation to the suppressive phenotype by CRP treatment the cells would be washed with physiological buffered saline prior to injection into the patient. The actual cell number transferred would range from about $10^4$ to about $10^8$ cells, about $10^5$ to $10^8$ cells, about $10^5$ to $10^8$ cells.

It will likely not require the separation of the monocyte population from the peripheral blood mononuclear cell population. In other words one would make a buffy coat of the patients cells and treat them (before or after activation). The presence of the other cells does not prevent and may enhance the effectiveness of the treatment.

The concentration of immature macrophages or dendritic cells which are activated (to produce suppressive macrophages or dendritic cells) by the CRP varies as a function of the purity of the cell sample used, but ranges from about $5 \times 10^4$ to about $1 \times 10^8$ per ml, preferably at least about $1 \times 10^6$, about $1.5 \times 10^6$ per ml, depending on the purity of the monocyte/macrophage cell population used to produce the suppressive macrophages and/or dendritic cells. Once activated, the suppressive macrophages and/or dendritic cells are washed and then administered in the patient's serum or saline, alone or in combination with an excipient or other additive. The activated cells are administered intravenously in saline at a concentration ranging from about $5 \times 10^4$ per ml, at least about $1 \times 10^5$ up to about $1 \times 10^6$ per ml. CRP or a CRP-related compound and/or other agents as otherwise described herein may be coadministered to the patient along with an effective amount of suppressive macrophages and/or dendritic cells. The suppressive macrophages and/or dendritic cells may be administered along with peripheral blood cells (preferably autologous peripheral blood cells) or as purified macrophages and/or dendritic cells.

The CRP used may be recombinant CRP, or CRP purified from a number of sources. For example, human CRP may be purified from human pleural effusion fluid. T. W. Du Clos, "C-reactive protein reacts with the U1 small nuclear ribonucleoprotein," *J. Immunol.* 143:2553-2559 (1989). For example, human pleural fluids may be obtained from discarded drains of patients undergoing surgery. The fluids may be clarified by high speed centrifugation. The CRP may be partially purified by affinity chromatography on PC-Sepharose and then may be further purified by gel filtration chromatography. The CRP may then be further purified by affinity chromatography on PC-Sepharose. For final purification, the protein may be purified by mono Q based FPLC. A major band should be seen at about 25 kDa on SDS-PAGE. The final preparation may then be filter-sterilized and endotoxin contamination may be measured by a limulus-based assay from Cambrex (East Rutherford, N.J.). Endotoxin may be removed using Acticlean Etox (Sterogene Bioseparations Inc., Carlsbad, Calif.) to reduce preparations to less than 0.3 ng of endotoxin/mg of protein.

Alternatively, CRP may be produced as a recombinant protein following general procedures well known in the art. U.S. Pat. No. 5,702,921 to Tanaka describes the production of human C-reactive protein using *Escherichia coli* vectors described therein. Recombinant CRP may also be produced using a baculovirus expression system as described in Marnell et al. *Protein Expression and Purification* 6:439, 1995.

The term "suppressive macrophages" or "suppressive dendritic cells" is used to describe a sample of monocyte/macrophages or dendritic cells (which may be included in a monocyte fraction or a peripheral blood fraction) that has been exposed to effective concentrations of CRP or a CRP-related compound in providing suppressive macrophages or dendritic cells according to the present invention. It is noted that in certain instances the term "activated dendritic cells" may be used synonymously with the term "suppressive dendritic cells". Suppressive macrophages or dendritic cells may be obtained from splenic cells, bone marrow-derived macrophages or peripheral blood cells (preferred, when the patient is a human). The cells utilized in the present invention are preferably autologous with the patient. The peripheral blood cells that are useful are the monocytes (representing about 10-20% of the peripheral blood cells), which group of cells excludes granulocytes and lymphocytes. These may be obtained by various separation and centrifugation techniques, which are well known in the art. See, for example, United States Patent Application publication US 2004 038398 A1, issued as U.S. Pat. No. 7,273,753, relevant portions of which are incorporated by reference herein.

Obtaining peripheral blood cells and in particular, a monocyte fraction is routine within the art. In order to produce non-activated immature macrophage cells, the peripheral blood cells are exposed to growth factors (e.g., human macrophage colony stimulating factor or M-CSF) in a cell growth medium (differentiation medium) and thereafter, are exposed to effective concentrations of CRP or a CRP-related compound in effective amounts. Any method for obtaining monocytes/macrophages may be used in the present invention. The monocytes/macrophages may be separated at an early step in the procedure and exposed to CRP as isolated immature monocytes/macrophages to produce suppressive macrophages which are then administered to a patient in need, or alternatively, the peripheral blood fraction containing immature monocytes/macrophages may be exposed to effective concentrations of CRP and/or a CRP-related compound as otherwise described herein to produce suppressive macrophages in the peripheral blood fraction with or without separation/purification of the suppressive macrophages for administration into a patient in need in effective amounts.

In general, peripheral blood cells or bone marrow cells are obtained and are initially exposed to macrophage colony stimulating factor (M-CSF) in a cell differentiation medium as otherwise described herein for a period of time sufficient to produce monocytes/immature macrophage cells which express the cell surface marker F4/80+. Subsequently, the immature macrophage cells are then exposed to effective concentrations of CRP in a differentiation medium to produce suppressive macrophages. Optionally, prior to exposure to CRP, the immature macrophages may be exposed in differentiation medium to effective concentrations (about 25 to 800 U/ml, about 100 to 600 U/ml, about 250 to 500 U/ml, about 400 U/ml) of gamma interferon (γIFN)).

In the case of generating suppressive mouse macrophages, in this method mouse bone marrow macrophages (BMM) are prepared as described in Mold, C., H. D. Gresham and T. W. Du Clos. 2001, *Journal of Immunology* 166:1200-1205. In brief, to prepare bone marrow macrophages (BMM), mice are killed, femurs are isolated under sterile conditions, the ends of the femurs are excised and bone marrow is flushed from the femurs in HBSS (Hanks balanced salt solution) with 0.2% human serum albumin (HSA). Cells are resuspended in 12-15 ml DMEM (Dulbecco's minimum essential medium) containing 2% FBS (fetal bovine serum) and 2% L cell conditioned medium (LCM, source of M-CSF) and allowed to adhere to tissue culture dishes for 2 h. At this time nonadherent cells are removed and put into culture in tissue culture flasks in DMEM, 2% FBS, 15% LCM. Nonadherent cells are removed after overnight culture and cultures are maintained in the same medium with feeding every 4 days. BMM are used after 7-14 days in culture. (Recombinant M-CSF may be substituted for L cell conditioned medium at a preferred concentration of 10 ng/ml, range of about 1 ng/ml to about 25 ng/ml or more). After 7 days, cells are 95% positive for the macrophage surface marker, F4/80 (Serotec). To generate suppressive macrophages, 7-14 day BMM are treated for 24 h with 100 U/ml recombinant mouse gamma interferon (IFN-γ). The macrophages are detached using 5 mM EDTA in PBS, washed into RPMI and treated with CRP at a concentration of 50-500 μg/ml for 30 min at 37° C. CRP-treated macrophages are washed twice with RPMI and injected into recipient mice.

In the case of generating human suppressive macrophages, the following exemplary approach may be taken. An exemplary method of generating suppressive human monocytes using PBMC (peripheral blood mononuclear cells) involves the steps of
1. Collecting sufficient quantities of blood from a patient (human);
2. Layering a sample of blood over a quantity of Mono/Poly solution (a cell separation medium from MP Biomedicals) and adding 0.2 ml of Hanks Balanced saline solution;
3. Centrifuging at 1400 RPM for 25 min at 22 C (room temperature) with the brake off;
4. Removing the plasma layer from the centrifuged sample as waste (yellow);
5. Removing the mononuclear cells (top cloudy layer containing monocytes) and placing in 50 ml sterile tube and washing with an appropriate amount (e.g. 15-40 ml) of PBS;
6. Washing 2× with PBS
    a. Centrifuging the sample for 10 min at 1250 RPM and 22 C.
7. Counting cells
8. Centrifuging cells
9. Resuspending cells at 5×106/ml in RPMI with 5% FBS; and Treating cells in culture with 100-200 μg/ml CRP for 20-24 h. These suppressive macrophage cells may be used to treat SLE and/or ITP accordingly, in the method of the present invention. The CRP-treated monocytes show decreased inflammatory cytokine responses to endotoxin (LPS) and increased IL-10 responses.

Purified monocytes also may be obtained from PBMC by positive selection on anti-CD14 magnetic beads (Miltenyi). The recovery is about 20% of the PBMC and the cells are > 90% monocytes (CD14+).

Human macrophages also may be generated from PBMC following the method of Mold, et al., 2002 *Journal of Autoimmunity* 19:147-154, relevant portions of which are incorporated by reference herein. In brief, PBMC are obtained as above and cultured for 3 days in Teflon dishes in IMDM (Iscove's modified Dulbecco's medium) with 10% heat inactivated human AB serum. Macrophages are then allowed to adhere to 24-well tissue culture plates for 1 h, washed to remove non-adherent cells and cultured for an additional 3 days in the same medium. These cells can then be used in the same way as mouse BMM-treated with IFN-γ for 24 h and then with CRP or simply treated with CRP. These cells are adherent, phagocytic and have macrophage markers (CD11b). Other methods for generating suppressive macrophages are also known in the art.

The term "differentiation medium" refers to a cell medium or environment (generally, a basal cell media) which is utilized to differentiate the peripheral blood cells of the present invention into non-activated immature macrophage cells prior to activating the cells with CRP to produce suppressive macrophages according to the present invention. In accordance with the invention the cell differentiation medium (basal cell medium) to form the non-activated immature macrophage cells may contain a variety of components as described including an effective amount of macrophage colony stimulating factor (M-CSF) and includes such media as, for example, RPMI1640, Dulbecco's Modified Eagle's Medium (DMEM), Ham's F12 medium (especially DMEM/F12 50:50), FCS (fetal calf serum) and growth factors, including GDF (growth and differentiation factor) and insulin-like growth factor. The cell differentiation medium may also contain supplements such as L-Glutamine, NEAA (non-essential amino acids), P/S (penicillin/streptomycin), gentamicin, N2 and β-mercaptoethanol (β-ME), among others. The same medium as described above, with minor variation (for example, excluding M-CSF) may be used to activate (activating medium) the resulting non-activated immature macrophage cells with effective amounts of CRP. To activate the immature macrophage cells to produce suppressive macrophages, an effective concentration of CRP or a CRP-related compound is used, as otherwise described herein.

The term "coadministration" or "combination therapy" is used to describe a therapy in which at least two active compounds in effective amounts are used to treat systemic lupus erythematosus a related disease state, condition or manifestation at the same time. Although the term coadministration preferably includes the administration of two active compounds to the patient at the same time, it is not necessary that the compounds be administered to the patient at the same time, although effective amounts of the individual compounds will be present in the patient at the same time.

"Naturally occurring" refers to an endogenous chemical moiety, such as a polypeptide or polynucleotide sequence or a carbohydrate, i.e., one found in nature. Processing of naturally occurring moieties can occur in one or more steps, and these terms encompass all stages of processing. Conversely, a "non-naturally occurring" moiety refers to all other moieties, i.e., ones that do not occur in nature, such as recombinant polynucleotide sequences and non-naturally occurring carbohydrates.

In the present invention, macrophages which express the cell surface marker F4/80+ (in the mouse) are exposed to effective concentrations of CRP (at about 10 µg per ml to about to 1 mg per ml or higher, preferably about 100 µg per ml to about 500 µg per ml, preferably about 100 µg per ml to about 300 µg per ml, including about 200 µg per ml) in cell growth medium for a period sufficient to activate the immature macrophages prior to administration. The suppressive macrophages or dendritic cells may be administered in the patient's serum or in saline, alone as purified cell fractions (purified to varying degrees from peripheral blood) or in an unpurified peripheral blood sample or in combination with an excipient or other additive. The cells preferably are administered intravenously in saline.

The concentration of non-activated immature macrophage and/or dendritic cells which are activated by the CRP or the CRP-related compound varies as a function of the purity of the cell sample used, but ranges from about $5 \times 10^4$ to about $1 \times 10^7$ per ml, at least about $1 \times 10^3$, about $1 \times 10^6$ per ml, depending on the purity of the immature cell population used. Once activated, the cells are washed and then administered in the patient's serum or preferably saline, alone or in combination with an excipient or other additive. The activated cells are administered intravenously in saline at a concentration ranging from about $5 \times 10^4$ per ml, at least about $1 \times 10^3$ up to about $1 \times 10^6$ per ml, alone or optionally, in combination with CRP or a CRP-related compound and optionally, another agent typically used to treat SLE or ITP as otherwise described herein.

According to various embodiments, the compounds/compositions according to the present invention may be used for treatment or prevention purposes in the form of a pharmaceutical composition. This pharmaceutical composition may comprise one or more of an effective amount of suppressive macrophages alone or in combination with CRP (preferably pure or recombinant CRP) and/or a CRP-related compound and optionally, at least one additional agent traditionally used to treat SLE or ITP, as otherwise described herein. CRP-related compounds may also be included. For example, the pharmaceutical composition may comprise an effective amount of suppressive macrophages, and a mixture of CRP and a CRP-related compound, suppressive macrophages and one or more additional agents such as anti-inflammatory drugs (NSAIDs) including traditional NSAIDs, COX-2 inhibitors and salicylates (such as aspirin), anti-malarials such as hydroxychloroquine, quinacrine, corticosteroids such as prednisone (Deltasone), betamethasone (Celestone), methylprednisolone acetate (Medrol, Depo-Medrol), hydrocortisone Cortef, Hydrocortone) and dexamethasone (Decadron, Hexadrol), among others and immunosuppressants such as methotrexate (Rheumatrex), cyclophosphamide (Cytoxan), Azathioprine (Imuran) and mycophenolate mofetil (MMF, also CellCept). In the case of the treatment of ITP, such treatments may preferably include a corticosteroid or an immunosuppressant (as described above). Preferred agents to be used for ITP treatment include dexamethasone or prednisone.

The pharmaceutical composition may also comprise a pharmaceutically acceptable excipient, additive or inert carrier. The pharmaceutically acceptable excipient, additive or inert carrier may be in a form chosen from a solid, semi-solid, and liquid, which are chosen to facilitate the administration of suppressive macrophage and/or dendritic cells as otherwise described herein without impacting the activity of the cells.

The pharmaceutical composition may be in a form chosen from sterile isotonic aqueous solutions, and compositions that include a patient's serum in combination with a pharmaceutically acceptable excipient or additive. In one embodiment, the administration route is intravenous.

The subject or patient may be chosen from, for example, a human, a mammal such as domesticated animal, or other animal. The subject may have one or more of the disease states, conditions or symptoms associated with SLE or ITP.

The compounds according to the present invention may be administered in an effective amount to treat or reduce the likelihood of SLE or ITP, and/or any one or more of the disease states, conditions or symptoms associated with SLE including, for example serositis, malar rash (rash over the cheeks and bridge of the nose), discoid rash (scaly, disk-shaped sores on the face, neck and chest), sores or ulcers (on the tongue, in the mouth or nose), arthritis, hemolytic anemia, low lymphocytic count, low platelet count, the presence of antinuclear bodies in the blood, skin lesions, CNS effects (including loss of memory, seizures, strokes and psychosis), lung symptoms/effects including inflammation (pleuritis), chronic pneumonitis, chronic diffuse interstitial lung disease and scarring of the lungs, hair loss, Raynaud's syndrome, lupus nephritis and sensitivity to light, fatigue, fever, nausea, vomiting, diarrhea, swollen glands, lack of appetite, sensitivity to cold (Raynaud's phenomenon) and weight loss, or, in the case of ITP, bleeding, red dots on the skin, red dots on the mouth membranes, purplish mouth membrane areas, bleeding nose, bleeding gum, digestive bleeding, urinary bleeding and brain bleeding. In the case of ITP, there is an increased platelet count pursuant to successful therapy. One of ordinary skill in the art would be readily able to determine an effective amount of cells, compounds or compositions to be administered and used for treatment by taking into consideration several variables including, but not limited to, the animal subject, age, sex, weight, site of the disease state or condition in the patient, previous medical history, other medications, etc.

It is noted here that administration of cells, compounds (CRP or CRP-related compounds) or compositions (which may include cells and/or CRP or CRP-related compounds and optionally, other agents) may be intermittent and will depend upon the patient's response to therapy. Thus, favorable response to therapy may require a single dose or multiple doses and further therapy may require therapy to be administered to the patient at varying intervals depending upon the patient's response to therapy, which can be readily measured. In the case of ITP, favorable therapy will reflect increased platelet counts as well as amelioration/reduction in one or more of the symptoms of bleeding, red dots on the skin, red dots on the mouth membranes, purplish mouth membrane areas, bleeding nose, bleeding gum, digestive bleeding, urinary bleeding and brain bleeding.

In the case of therapy for SLE or ITP, the dose of suppressive macrophages (activated cells) for a human patient is that which is an effective amount and may range from as little as $1 \times 10^4$ activated cells, at least $1 \times 10^5$ cells, between $1 \times 10^6$ and $1 \times 10^7$ cells, depending upon the purity of the activated cells used in the pharmaceutical formulation. The cells may be combined with CRP or a CRP-related compound at levels ranging from about 100 µg to at least about 500 µg or more, which may be administered in a manner consistent with the delivery of the drug and the disease state or condition to be treated. In treating SLE, ITP or related symptoms, conditions and/or disease states, CRP or a CRP-related compound, may be administered alone or may be coadministered with suppressive macrophages orally (although suppressive macrophages are administered intravenously preferably in saline solution). When used, the amount of CRP which is administered to a human patient preferably ranges from about 0.05 mg/kg to about 25 mg/kg, about 0.1 mg/kg to about 10 mg/kg, about 0.1 mg/kg to about 7.5 mg/kg, about 0.25 mg/kg to about 5-6 mg/kg., about 1.25 to about 5.7 mg/kg. Typical dosages for a 70 kg patient therefore include a dose of about 5-10 mg to about 1.5 grams or more, about 100 mg to about 850 mg, about 500 to about 700 mg. The amount of CRP-related compound that may be administered is an effective amount, which may fall outside of the range for administration of CRP (especially at the low end), given that the molecular weight of these compounds tends to be significantly lower than for CRP itself.

The dose of a formulation according to the present invention may be administered prior to the onset of ITP or SLE, at the start of evidence of symptomology, when ITP symptoms are full blown, during SLE flares or during remission prior to an expected flare. For example, the dose may be administered for the purpose of treating and/or reducing the likelihood of any one or more of these disease states, symptoms or conditions occurs or manifests, including serositis, malar rash (rash over the cheeks and bridge of the nose), discoid rash (scaly, disk-shaped sores on the face, neck and chest), sores or ulcers (on the tongue, in the mouth or nose), arthritis, hemolytic anemia, low lymphocytic count, low platelet count, the presence of antinuclear bodies in the blood, skin lesions, CNS effects (including loss of memory, seizures, strokes and psychosis), lung effects including chronic pneumonitis and scarring of the lung, hair loss, Raynaud's syndrome, lupus nephritis, sensitivity to light, fatigue, fever, nausea, vomiting, diarrhea, swollen glands, lack of appetite, sensitivity to cold (Raynaud's phenomenon), weight loss, and hair loss. The dose may be administered prior to diagnosis, but in anticipation of SLE or anticipation of flares. The dose also is preferably administered during flares to reduce the severity of same. In the case of ITP, the compositions are administered to relieve or reduce one or more of the conditions of bleeding, red dots on the skin, red dots on the mouth membranes, purplish mouth membrane areas, bleeding nose, bleeding gum, digestive bleeding, urinary bleeding and brain bleeding, to reduce antibodies associated with the disease and to increase platelet numbers/counts (for example, by reducing platelet clearance). In addition, for the treatment of ITP as described above, pharmaceutical compositions comprising CRP or a CRP-related compound in the absence of suppressive macrophages and optionally, including an agent which is typically used for treating ITP or its symptomology, may be included in the composition. These represent preferred embodiments for the treatment of ITP.

SLE is a multisystem disease characterized by nephritis, skin disease and autoimmune hematologic disease. C-reactive protein (CRP) is an acute phase protein that is underexpressed in inflammation associated with SLE. Recent genetic studies show an association between increased risk of SLE and genotypes expressing low CRP levels. The inventors have recently shown that CRP is protective from nephritis and mortality in two mouse models of SLE. The mechanism for the protection remains undetermined. IVIG has been shown to decrease disease activity in both SLE and the related condition immune thrombocytopenia (ITP). Very recently, Siragam et al. have shown that treatment of spleen cells in vitro generates a dendritic cell (DC) that can adoptively transfer suppression of ITP to normal mice. This effect was dependent on the expression of an activating Fc receptor, FcγRI, III or IV in the donor cells and the inhibitory receptor FcγRIIb in the recipient. The present inventors identified FcγRI and FcγRIIb in the mouse as the receptors for CRP. The present inventors have found that CRP treatment of spleen cells in culture also induces a cell (suppressive macrophage) that can transfer suppression of ITP. This adoptive transfer model will allow the identification of the cells through which CRP mediates suppression of ITP and possibly SLE.

EXAMPLES

Experimental design and methods. The inventors have established a passive model of immune thrombocytopenic purpura (ITP). C57B1/66 mice are treated with 5 µg of anti-platelet antibody (anti-CD41) at time 0, resulting in a decrease in platelets from $1000 \times 10^6/mm^3$ to approximately $300 \times 10^6/mm^3$ by 24 h (FIG. 2). To generate regulatory cells, spleen cells from naïve mice are treated with 18 mg/ml of IVIG or 200 µg/ml of CRP for 30 min in culture. The spleen cells are washed and injected intravenously into mice, which are treated with anti-CD41 24 h later. Platelets are counted at time 0 and at 24 h.

Reagents: CRP purified from human pleural fluid by affinity chromatography, gel-filtration, ion exchange chromatography by FPLC and endotoxin removal (>99% purity, <3 EU/mg protein) (2); IVIG, Gamimmune N, 10% (Bayer); CD41-specific (integrin $a_{IIb}$) rat mAb (BD). Mice: C57BL/6 (B6) mice (NCI). Priming of spleen cells. Spleen cell suspensions are prepared, washed and incubated at $1.4 \times 10^6$ cells/ml with 18 mg/ml IVIG, 200 µg/ml CRP or 200 µg/ml BSA for 30 min at 37° C. in RPMI-1640, washed twice, resuspended to $5 \times 10^6$/ml and injected i.v. (200 µl/mouse). Induction and suppression of ITP. Mice are injected i.v. with primed spleen cells. After 24 h, ITP is induced by i.p. injection of 5 µg anti-CD41. After 24 h, mice are bled and platelets counted using Unopette dilutors and a hemocytometer.

Purification of cells. Cell types may be separated using positive selection and magnetic separation on an AutoMACS (Miltenyi Biotec, Auburn, Calif.). Because macrophages are identified as the required cell type, bone marrow cultures are subsequently used to generate these cell types in high purity.

Figure 5:
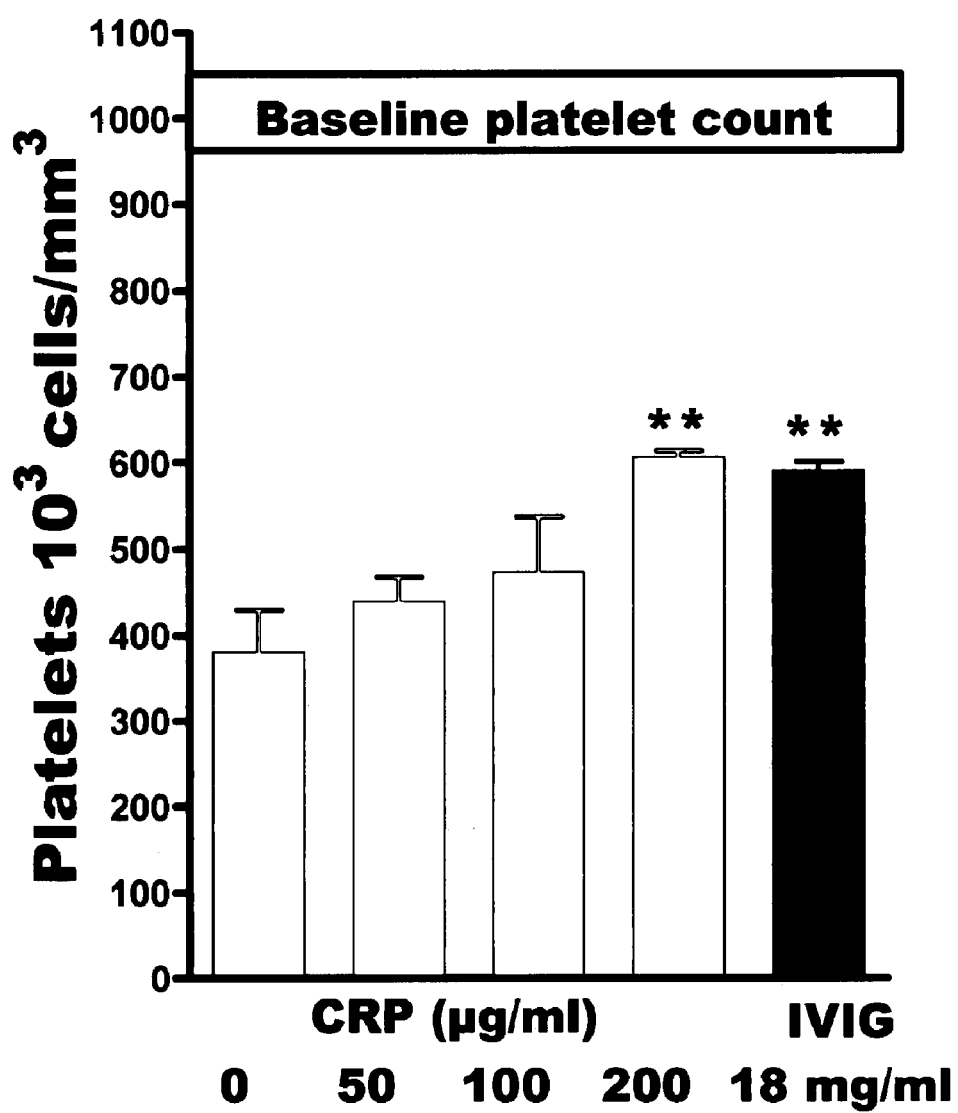
FIG. 5 shows the transfer of suppression of ITP following spleen cell treatment with 50, 100 and 200 μg/ml of CRP and 18 mg/ml of IVIG using the experimental design in FIG. 3A.
Figure 6:
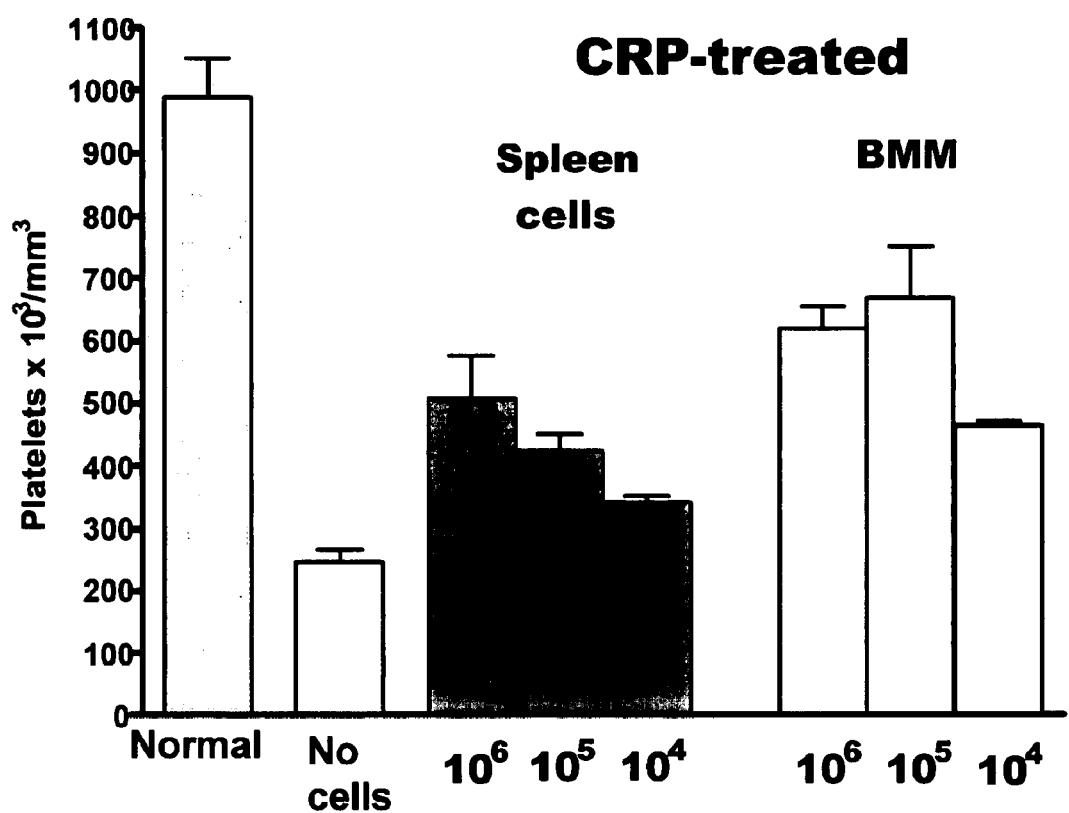
FIG. 6 shows that bone marrow macrophages could produce the same results as using spleen cells in the adoptive transfer approach of the present invention. This figure shows the cell dose response for transfer experiment. Spleen cells or bone marrow macrophages (BMM) were treated in vitro with CRP (200 μg/ml) for 30 min at 37° C. and washed. The indicated number of cells were injected i.v. into recipient mice. Recipients were treated 24 h later with 5 μg of anti-CD41 i.v. Blood samples were taken and platelets were counted before injection (normal) and 24 h later.

FIG. 3 "Adoptive Transfer of CRP-Mediated Suppression of ITP"—CRP treatment of B6 spleen cells ameliorates thrombocytopenia in ITP. Spleen cells were treated in vitro with CRP (200 µg/ml) or IVIG (18 mg/ml) for 30 min. Cells were washed and $10^6$ cells were injected i.v. into recipient mice. Recipients were treated 24 h later with 5 µg of anti-CD41. Platelets were counted before injection (shown as baseline) and 24 h later. Results are mean±SEM, n=3, *p<0.05. Representative of 4 experiments. Other figures reflect results obtained with varying concentrations of CRP (FIG. 5).

Current therapies for SLE use untargeted immunosuppression. Approaches that harness the immune system's natural regulatory pathways are promising alternatives with fewer side effects. The inventors have found an innate regulatory pathway triggered by C-reactive protein (CRP) binding to FcγR that effectively treats lupus nephritis in mice (second set of references 1a, 2a). However, the mechanisms involved are incompletely defined. IVIG has been used to treat both immune thrombocytopenia (ITP) and lupus nephritis. Siragam et al. have recently described an adoptive transfer model of IVIG treatment of ITP (second set of references, 3a). They had previously shown that IVIG ameliorates thrombocytopenia in this model. They have now determined that spleen cells, and specifically, dendritic cells (DC), treated with IVIG in vitro act through FcγR to transfer suppression to mice treated to induce ITP. The finding that CRP also induces cells capable of adoptive transfer of protection from ITP provides a unique opportunity to identify the mechanisms involved in immunomodulation by CRP. This is the first described adoptive transfer model of immunomodulation by CRP. Although IVIG is an effective treatment for ITP, and to a lesser degree, SLE, it has several limitations. It must be used in very high doses in vivo and it is expensive. It may occasionally exacerbate disease, either due to aggregates or interaction with FcγRIII. CRP has the advantage of being easy to produce by recombinant technology and is therefore virus free and less expensive. CRP does not interact with the proinflammatory receptor, FcγRIII. In the studies reported here, CRP was effective in vitro and in vivo at 200 µg/ml whereas IVIG was used at 18 mg/ml. These findings suggest that immunoregulation induced by CRP is a promising novel approach to treatment of ITP and SLE.

This work is directly related to the treatment of SLE or ITP with agents that can alter the immune system. The inventors have shown that CRP inhibits SLE in mouse models and assert that the use of CRP to treat human lupus nephritis and/or ITP is a viable option. The experiments described herein and to be conducted based upon same are significant in two major ways. Firstly, they define the mechanisms involved in immunoregulation by CRP and by IVIG. Although it has been known that CRP downregulates inflammation in several animal models, the mechanisms involved have not been defined (4a). Establishing an adoptive transfer model of CRP-initiated immunomodulation assist in dissecting these mechanisms. Not only would these results allow for the further development of CRP as a therapeutic agent, but they also may lead to the development of other biologicals that act in a similar manner to initiate a regulatory pathway to treat SLE and/or ITP.

SLE is an autoimmune disease characterized by multiple systemic manifestations including renal disease, skin disease, and hematological involvement. The inventors demonstrated in two SLE mouse models that injection of CRP increases survival and protects from renal disease. Survival was prolonged up to 3 months after a single injection of CRP (1a, 2a). Notably, CRP was equally effective when administered during active renal disease. The protective mechanisms are incompletely understood but it is speculated that a long-lived suppressive cell (possibly a regulatory T cell (2a)) is generated by CRP treatment. The inventors have now determined that CRP-treated spleen cells adoptively transfer suppression of ITP, similar to IVIG. This model provides the first opportunity to identify and characterize the initial cell activated by CRP treatment and makes it possible to identify the pathways involved in vivo. The inventors have determined that the suppressive cell is a suppressive macrophage cell. The preliminary data show that treatment of spleen cells with CRP in vitro generates macrophage cells that ameliorate ITP (FIG. 3). The experiments are based on the studies described for the use of IVIG to treat ITP in mice (3a). The inventors have established this model of ITP. C57BL/6 mice are treated with anti-CD41 at time 0, resulting in a decrease in platelets from $1000 \times 10^6/mm^3$ to approximately $300 \times 10^6/mm^3$ by 24 h (3a). To generate regulatory cells, spleen cells from naïve mice are treated in vitro with 18 mg/ml of IVIG or 200 µg/ml of CRP for 30 min. The spleen cells are washed and injected i.v. into mice, which are treated with anti-CD41 24 h later. Platelets are counted at time 0 and at 24 h. The results are shown in FIG. 3B, C.

As expected, transfer of IVIG-treated cells prevented thrombocytopenia 24 h after treatment. CRP-treated cells caused a nearly identical level of protection from ITP. Cells treated with a control protein did not transfer suppression (FIG. 3C and (3a)). These experiments clearly establish the protective effect of CRP on this model of ITP. These experiments further identify the cell involved in the adoptive transfer of suppression, the receptors that mediate the interaction between CRP and the cell, and the effects of CRP treatment on cell surface markers and gene expression.

A first approach was to identify the cells that are responsible for transferring protection. The inventors initially focused on the dendritic cells as dendritic cells were responsible for IVIG-mediated adoptive transfer. Spleen cells are treated with CRP or IVIG and dendritic cells are enriched using a CD11c positive selection kit. CD11c-enriched and CD11c-depleted cells are then be injected to test CD11c-enrichment of spleen cells did not increase the effectiveness of CRP treatment. It was further showed that depletion of macrophages from mice prior to spleen cell isolation eliminated the CRP-mediated suppression of ITP. The inventors then used standard methods to prepare purified bone marrow-derived macrophages (>95% F4/80+). These macrophages, when treated for 24 h with γIFN, and then treated with CRP were highly effective in suppressing ITP in a recipient mouse. These studies identify the macrophage as the cell with which CRP reacts as well as the cell responsible for transferring suppression. It was also shown that the peripheral blood cells obtained from a human patient capable of being activated and used in the present invention are monocytes expressing the marker CD14, which may be activated to produce suppressive macrophages.

Figure 4:
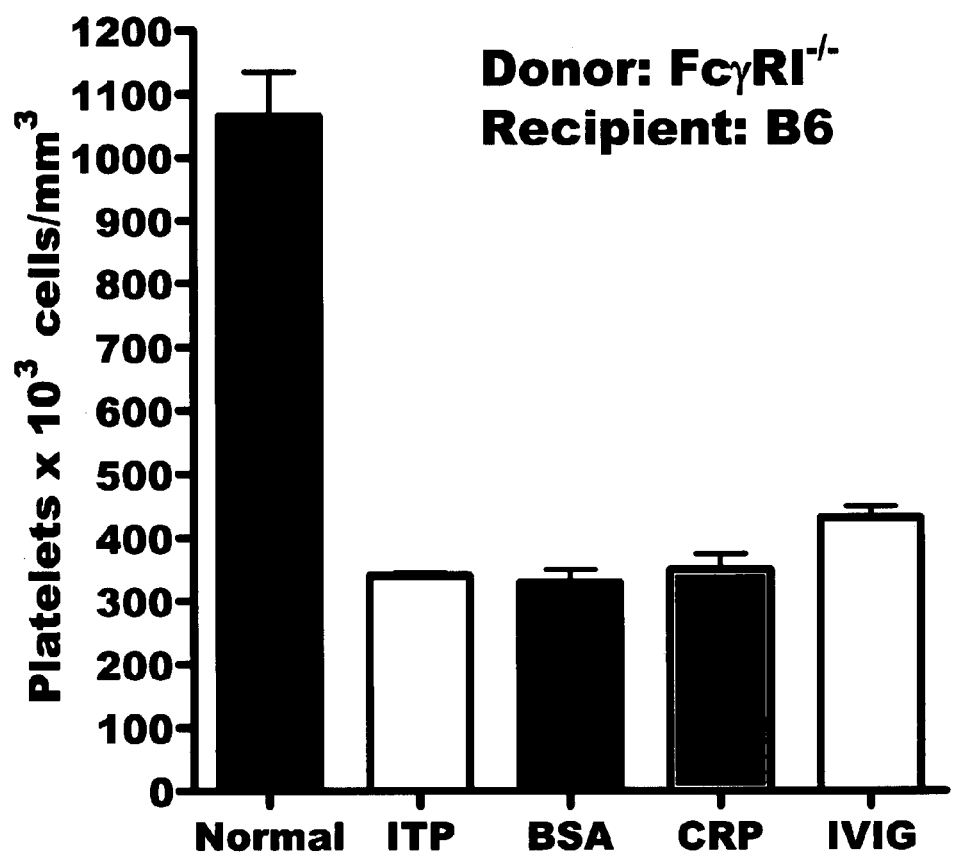
FIG. 4 shows that spleen cells from mice deficient in FcγRI and treated with CRP and IVIG and transferred as in FIG. 3 fail to suppress ITP to normal recipient mice.

The role of FcγR in this process (FIG. 4) was also determined. In the case of IVIG, the cell that is capable of transferring suppression is FcR γ-chain positive. As it has been shown that the major FcγR that bind CRP are FcγRI and FcγRII (5a, 6a) the role of these two receptors was tested. FcγRI$^{-/-}$ mice were obtained. If CRP interaction with FcγRI is required for this effect, cells from these mice will not transfer suppression. Also tested are the ability of spleen cells from γ-chain$^{-/-}$ mice to mediate suppression. If cells from these mice fail to transfer suppression, it indicates a requirement for an activating FcγR (FcγRI, FcγRIII or FcγRIV) similar to the requirements of IVIG. The present examples evidence that FcγRI and FcR γ chain are required on donor spleen cells for CRP transfer of suppression (FIG. 4 and not shown). Siragam et al. (3a, second set of references) have shown that the inhibitory receptor FcγRIIb is not required for IVIG-mediated adoptive transfer although FcγRIIb is required in the recipient mouse. Therefore, testing FcγRIIb$^{-/-}$ mice in combination with C57BL/6 mice for their ability to act as donors and recipients of ITP suppression is performed. The examples show that FcγRIIb is required in the recipient, but not in the donor spleen cells for CRP transfer of suppression (not shown).

The experiments focus on the identification of the cell and receptors required by CRP to induce a suppressive phenotype. It is also an objective to characterize the response of the cells to CRP and the interaction of the cells with the recipient. Preliminary experiments give us more insight into mechanisms by which CRP induces immunomodulation. The cells identified will be the target of experiments designed to characterize the changes in these cells induced by CRP. One approach will be to examine the cytokine profile induced by CRP treatment using gene array. Cells treated with IVIG, CRP or BSA controls are tested by a GE superarray as previously done in peritoneal cells. The cytokines identified will be quantitated by qRT-PCR. The cytokine requirements could then be examined in mice deficient in the identified cytokines and/or their receptors. The second approach examines the change in cell surface markers induced by CRP.

Methods: Reagents: CRP purified from human pleural fluid by affinity chromatography, gel-filtration, ion exchange chromatography by FPLC and endotoxin removal (>99% purity, <3 EU/mg protein). IVIG: Gamimune N, 10% (Bayer); CD41-specific (integrin $a_{IIb}$) rat mAb (BD). Mice: C57BL/6 (B6) mice (NCI); FcγR2b$^{-/-}$ and C3$^{-/-}$ mice, FcγR1$^{-/-}$ mice and FceR1γ$^{-/-}$ mice (Taconic) all on B6 background. Priming of spleen cells: Spleen cell suspensions are prepared, washed and incubated at $1.4 \times 10^6$ cells/ml with 18 mg/ml IVIG, 200 µg/ml CRP or 200 µg/ml BSA for 30 min at 37° C., washed twice, resuspended to $5 \times 10^6$/ml and injected i.v. (200 µl/mouse). Induction and suppression of ITP. Mice are injected i.v. with primed cells. After 24 h, ITP is induced by i.p. injection of 5 µg anti-CD41. After 24 h, mice are bled and platelets counted. Purification of cells: Cell types are separated using magnetic separation on an AutoMACS (Miltenyi).

Further Experiments

Experimental design and methods. These further studies used a passive model of ITP. C57BL/6 mice are treated with 5 µg of anti-platelet antibody (anti-CD41) at time 0, resulting in a decrease in platelets from $1000 \times 10^6$/mm$^3$ to approximately $300 \times 10^6$/mm$^3$ by 24 h. To generate suppressive cells, spleen cells from naïve mice are treated with 18 mg/ml of IVIG or 200 µg/ml of CRP for 30 min in culture. The spleen cells are washed and injected i.v. into mice, which are treated with anti-CD41 to induce ITP 24 h later. Platelets are counted at time 0 and at 24 h.

Reagents: CRP is purified from human pleural fluid by affinity chromatography, gel-filtration, ion exchange chromatography by FPLC and endotoxin removal (>99% purity, <3 EU/mg protein); IVIG, Gamimune N, 10% (Bayer); CD41-specific (integrin $α_{IIb}$) rat mAb (BD). Mice: C57BL/6 (B6) mice (NCI)

Priming of spleen cells. Spleen cell suspensions are prepared, washed and incubated at $1.4 \times 10^6$ cells/ml with 18 mg/ml IVIG, 200 µg/ml CRP or 200 µg/ml BSA for 30 min at 37° C. in RPMI-1640, washed twice, resuspended to $5 \times 10^6$/ml and injected i.v. (200 µl/mouse).

Preparation and priming of bone marrow macrophages (BMM). Cells are isolated from mouse bone marrow and differentiated into macrophages (BMM) by culture in complete DMEM with 5% FCS. 10% L-cell conditioned medium is added as a source of M-CSF. After 7-14 days in culture BMM are treated for 24 h with 100 U/ml γIFN. Cells are removed from dishes with 0.5 mM EDTA in PBS, washed into RPMI and treated with CRP or IVIG as described for spleen cells.

Induction of ITP. ITP is induced by i.p. injection of 5 µg anti-CD41. After 24 h, mice are bled and platelets counted using Unopette dilutors and a hemocytometer. Transfer of 10$^6$ CRP-treated spleen cells or $10^5$-$10^6$ CRP-treated BMM per mouse 24 h prior to injection of anti-platelet antibody is sufficient to reduce thrombocytopenia in recipients.

Direct treatment of ITP with CRP. CRP is injected i.v. 4 h prior to injection of anti-platelet antibody. A dose of 200-500 µg per recipient mouse (8-20 mg/kg) is sufficient to reduce thrombocytopenia in recipients.

Results

Experimental immune thrombocytopenia (ITP) was induced by intravenous (i.v.) injection of 2-5 µg/mouse of rat mAb to a mouse platelet antigen (BD Bioscience, anti-CD41). The method is based on the Siragam et al. paper. FIG. 2 shows the model from the data.

Spleen cell transfer protocol for suppression of ITP in this experiment was as follows. Spleens are removed from normal mice, separated into a single cell suspension, which is treated with CRP for 30 min., washed and injected i.v. into recipient mice. Twenty-four hours later ITP is induced in the recipients and platelet counts are measured initially and at the 24 h nadir. CRP-treated spleen cells were as effective as IVIG-treated spleen cells. FIGS. 3A 3B and 3C show the transfer protocol and results. The spleen cell transfer requires expression of FcγRI on the donor cells and FcγRII in the recipient. This experiment showed that 200 µg/ml of CRP was the equivalent of IVIG at 18/mg/ml at increasing platelets (see the same for FIG. 3). The transferred cell can be depleted from the spleen by treating the donor mouse with liposomes containing Clodronate. This indicates that the active cell is likely to be a macrophage.

Figure 7:
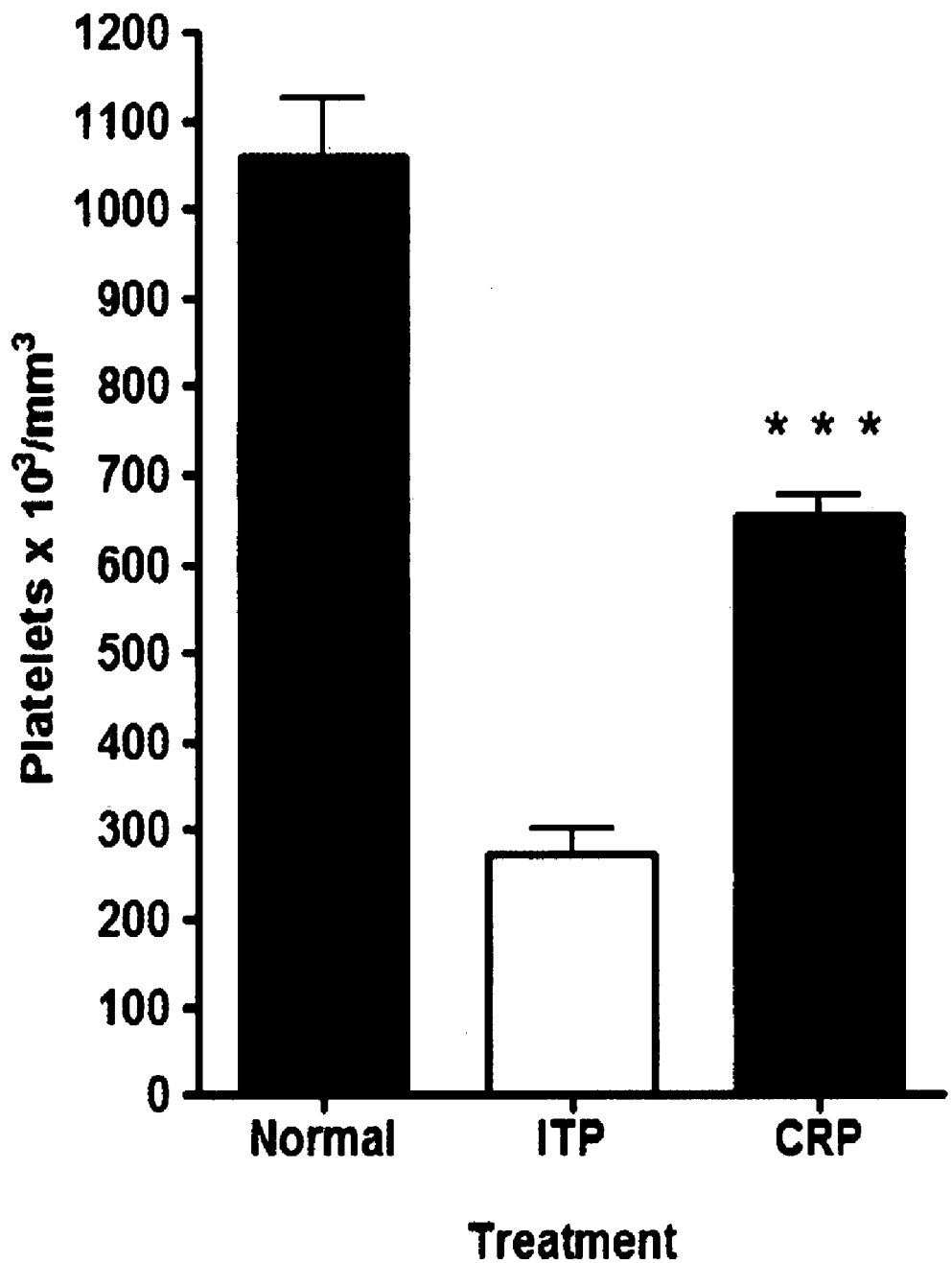
FIG. 7 shows that i.v. Injection of CRP (200 μg/mouse) 4 h prior to injection of anti-CD41 is effective in preventing thrombocytopenia.

The same effect of spleen cells can be reproduced using mouse bone marrow-derived macrophages (FIG. 7). Bone marrow cells are collected and cultured for 7-14 days in medium (Dulbecco's Modified Eagle's Medium or DMEM) containing appropriate growth factors and 5% FCS (M-CSF from L-cell conditioned medium-supplied as 10% by volume of the L-cell conditioned medium, which contains the growth factors in unspecified concentration) to induce differentiation into macrophages (BMM). Macrophages (>90% positive for macrophage marker F4/80) are treated for 24 h with interferon-gamma (100 U/ml) and then for 30 min with CRP. BMM (approximately 10$^5$-10$^6$ cells) are transferred into recipients and ITP is induced as for spleen cells. Note that fewer BMM cells may result in a higher concentration of suppressive macrophage cells compared to spleen cells and peripheral blood cells. FIG. 7 shows that a smaller number of CRP-treated BMM is needed to produce the same effect as CRP-treated spleen cells. This is consistent with the active cell being a macrophage, since spleen cells are <10% macrophages.

Experiments also showed that ITP can also be suppressed by i.v. injection of CRP 4 h prior to injection of anti-platelet antibody. An effective dose was 200 µg of CRP per mouse.

Mutant CRP (Y175L)

The contact residues between CRP and FcγR have been identified and a small number of mutant CRP molecules have been tested for binding to human FcγR using surface plasmon resonance (SPR). One of these mutants in which tyrosine 175 is replaced by leucine (Y175L CRP, SEQ ID No.: 6) has decreased binding to FcγRII and FcγRIII, but retains binding to FcγRI. Y175L CRP has also lost the ability to activate complement.

Figure 8A:
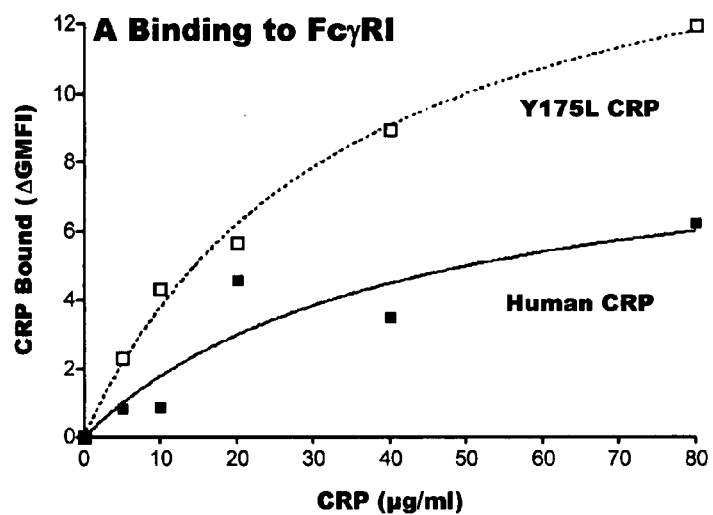
FIGS. 8A and 8B show the results of the binding of Y175L CRP, a candidate for selective anti-inflammatory activity, to mouse macrophages. Peritoneal exudate cells were isolated from C57BL/6 mice and incubated with purified human or recombinant mutant CRP (Y175L). CRP binding to macrophages was detected by two-color flow cytometry using anti-F4/80 to identify macrophages and FITC-2C10 mAb to detect CRP binding.
Figure 8B:
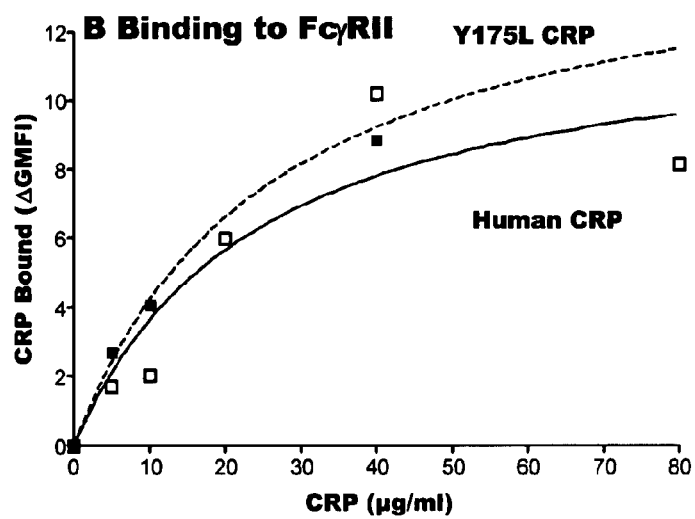

Y175L CRP is a candidate for selective anti-inflammatory activity, and was tested for its binding to mouse macrophages. In this experiment, peritoneal exudate cells were isolated from C57BL/6 mice and incubated with purified human or recombinant mutant CRP (Y175L). CRP binding to macrophages was detected by two-color flow cytometry using anti-F4/80 to identify macrophages and FITC-2C10 mAb to detect CRP binding. The results appear in FIGS. 8A and 8B. FIG. 8A shows the macrophages expressing FcγRI (from FcγRIIb$^{-/-}$ mice). FIG. 8B shows the macrophages expressing FcγRIIb (from FcR γ-chain$^{-/-}$ mice).

The results show that Y175L has increased binding to FcγRI on mouse macrophages and normal binding to FcγRIIb (FIG. 8). Thus, analysis of Y175L CRP shows an increased interaction with FcγRI relative to FcγRII in both human and mouse. Based upon the binding experiments, it is predicted that Y175L CRP will be more effective than native CRP in treating SLE and ITP as otherwise described herein.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

REFERENCES

First Group

1. Du Clos T W. Function of C-reactive protein. *Ann Med* 2000; 32:274-8.
2. Du Clos T W. The interaction of C-reactive protein and serum amyloid P component with nuclear antigens. *Mol Biol Rep* 1996; 23:253-60.
3. Volanakis J E. Human C-reactive protein: expression, structure, and function. *Mol Immunol* 2001; 38:189-197.
4. Gabay C, Roux-Lombard P, de Moerloose P, Dayer J-M, Vischer T, Guerne P-A. Absence of correlation between interleukin 6 and C-reactive protein blood levels in Systemic Lupus Erythematosus compared with Rheumatoid Arthritis. J Rheumatol 1993; 20:815-821.
5. Du Clos T W, Mold C. C-reactive protein: an activator of innate immunity and a modulator of adaptive immunity. *Immunol Res* 2004; 30:261-78.
6. Heuertz R M, Dongyuan X, Samols D, Webster R O. Inhibition of C5a des Arg-induced neutrophil alveolitis in transgenic mice expressing C-reactive protein. *Am J Physiol*, 1994; 266:L649-L654.
7. Heuertz R M, Piquette C A, Webster R O. Rabbits with elevated serum C-reactive protein exhibit diminished neutrophil infiltration and vascular permeability in C5a-induced alveolitis. *Am J Pathol* 1993; 142:319-328.
8. Xia D, Samols D. Transgenic mice expressing rabbit C-reactive protein are resistant to endotoxemia. *Proc Natl Acad Sci USA* 1997; 94:2575-80.
9. Mold C, Rodriguez W, Rodic-Polic B, Du Clos T W. C-reactive protein mediates protection from lipopolysaccharide through interactions with Fc gamma R. *J Immunol* 2002; 169:7019-25.
10. Szalai A J, Nataf S, Hu X-Z, Barnum S R. Experimental allergic encephalomyelitis is inhibited in transgenic mice expressing human C-reactive protein. *J Immunol* 2002; 168:5792-5797.
12. Gershov D, Kim S, Brot N, Elkon K B. C-reactive protein binds to apoptotic cells, protects the cells from assembly of the terminal complement components, and sustains an antiinflammatory innate immune response: implications for systemic autoimmunity. *J Exp Med* 2000; 192:1353-1363.
13. Mold C, Baca R, Du Clos T W. Serum amyloid P component and C-reactive protein opsonize apoptotic cells for phagocytosis through Fcy receptors. *J Autoimmun* 2002; 19:147-54.
14. Du Clos T W, Zlock L T, Hicks P S, Mold C. Decreased autoantibody levels and enhanced survival of (NZB× NZW) F1 mice treated with C-reactive protein. *Clin Immunol Immunopathol* 1994; 70:22-7.
15. Szalai A J, Weaver C T, McCrory M A, van Ginkel F W, Reiman R M, Kearney J F, Marion T N, Volanakis J E. Delayed lupus onset in (NZB×NZW)FI mice expressing a human C-reactive protein transgene. *Arthritis Rheum* 2003; 48:1602-11.
16. Rodriguez W, Mold C, Kataranovski M, Hutt J, Marvell L L, Du Clos T V Reversal of ongoing proteinuria in autoimmune mice by treatment with C-reactive protein. *Arthritis Rheum* 2005; 52:642650.
17. Theofilopoulos A N, Dixon F J. Murine models of systemic lupus erythematosus. *Adv Immunol* 1985; 37:269-391.
18. Du Clos T W. C-reactive protein reacts with the U1 small nuclear ribonucleoprotein. *J Immunol* 1989; 143:2553-9.
19. van Rooijen N, Sanders A. Liposome mediated depletion of macrophages: mechanism of action, preparation of liposomes and applications *J Immunol Methods* 1994; 174:83-93
20. Du Clos T W, Volzer M A, Hahn F F, Mao R, Mold C, Searles R P. Chromatin clearance in C57BU10 mice: interaction with heparan sulphate proteoglycans and receptors on Kupffer cells. *Clin Exp Immunol* 1999; 117:403-11.
21. Oldenhove G, de Heusch M, Urbain-Vansanten G, Urbain J, Maliszewski C, Leo 0, Moser M. CD4+ CD25+ regulatory T cells control T helper cell type 1 responses to foreign antigens induced by mature dendritic cells in vivo. *J Exp Med* 2003; 199:259-66.
22. Rubin R L. Enzyme-linked immunosorbent assay for anti-DNA and antihistone antibodies. In: Rose N R, Friedman H, Fahey J L, editors. Manual of Clinical Laboratory Immunology. Washington: ASM; 1986. p. 744-749.
23. Kikawada E, Lenda D M, Kelley V R. IL-12 deficiency in MRL-Faslpr) mice delays nephritis and intrarenal IFN-gamma expression, and diminishes systemic pathology. *J Immunol* 2003; 170:3915-25.
24. Smeenk R J, Brinkman K, van den Brink H G, Westgeest A A. Reaction patterns of monoclonal antibodies to DNA. *J Immunol* 1988; 140:378692.
25. McHugh R S, Shevach E M. Cutting edge: depletion of CD4+CD25+ regulatory T cells is necessary, but not sufficient, for induction of organ-specific autoimmune disease. *J Immunol* 2002; 168:597983.
26. Du Clos T V C-reactive protein as a regulator of autoimmunity and inflammation. *Arthritis Rheum* 2003; 48:1475-7.
27. Christensen S R, Kashgarian M, Alexopoulou L, Flavell R A, Akira S, Shlomchik M J. Toll-like receptor 9 controls anti-DNA autoantibody production in murine lupus. *J Exp Med* 2005; 202:321-331.
28. Zhou T, Bluethmann H, Eldridge J, Berry K, Mountz J D. Origin of CD4−CD8−B220+ T cells in MRL-lpr/lpr mice. Clues from a T cell receptor beta transgenic mouse. *J Immunol* 1993; 150:3651-67.
29. Tesch G H, Maifert S, Schwarting A, Rollins B J, Kelley V R. Monocyte chemoattractant protein 1-dependent leukocytic infiltrates are responsible for autoimmune disease in MRL-Faslpr) mice. *J Exp Med* 1999; 190:1813-24.
30. Walport M J. Lupus, DNase and defective disposal of cellular debris. *Nat Genet* 2000; 25:1356.
31. Kim S J, Gershov D, Ma X, Brot N, Elkon K B. Opsonization of apoptotic cells and its effect on macrophage and T cell immune responses. *Ann NY Acad Sci* 2003; 987:68-78.
32. Ehrenstein M R, Cook H T, Neuberger M S. Deficiency in serum immunoglobulin IgM predisposes to development of IgG autoantibodies. *J Exp Med* 2000; 191:1253-8.
33. Boes M, Schmidt T, Linkemann K, Beaudette B C, Marshak-Rothstein A, Chen J. Accelerated development of IgG autoantibodies and autoimmune disease in the absence of secreted IgM. *Proc Natl Acad Sci USA* 2000; 97:1184-9.

34. Botto M, Walport W. Clq, autoimmunity and apoptosis. *Immunobiology* 2002; 205:395-406.
35. Clynes R, Dumitru C, Ravetch J V. Uncoupling of immune complex formation and kidney damage in autoimmune glomerulonephritis. *Science* 1998; 279:1052-1054.
36. Balomenos D, Rumold R, Theofilopoulos A N. Interferon-gamma is required for lupus-like disease and lymphoaccumulation in MRL-lpr mice. *J Clin Invest* 1998; 101:364-71.
37. Heuertz R M, Xia D, Samols D, Webster R D. Inhibition of C5a des Arg-induced neutrophil alveolitis in transgenic mice expressing C-reactive protein. *Am J Physiol* 1994; 266:L649-L654.
38. Baltz M L, Rowe I F, Pepys M B. In vivo turnover studies of C-reactive protein. *Clin Exp Immunol* 1985; 59:243-50.
39. Hutchinson W L, Noble G E, Hawkins P N, Pepys M B. The pentraxins, C-reactive protein and serum amyloid P component, are cleared and catabolized by hepatocytes in vivo. *J Clin Invest* 1994; 94:1390-1396.
40. Carvalho-Pinto C E, Garcia M I, Mellado M, Rodriguez-Frade J M, Martin-Caballero J, Flores J, Martinez A C, Balomenos D. Autocrine production of IFN-gamma by macrophages controls their recruitment to kidney and the development of glomerulonephritis in MRL/lpr mice. *J Immunol* 2002; 169:1058-67.
41. Groux H, O'Garra A, Bigler M, Rouleau M, Antonenko S, de Vries J E, Roncarolo M G. A CD4+ T-cell subset inhibits antigen-specific T-cell responses and prevents colitis. *Nature* 1997; 389:737-42.

REFERENCES

Second Group

1a. Rodriguez, W., C. Mold, M. Kataranovski, J. Hutt, L. L. Marnell, and T. W. Du-Clos 2005. Reversal of ongoing proteinuria in autoimmune mice by treatment with C-reactive protein. *Arthritis Rheum* 52:642-650.
2a. Rodriguez, W., C. Mold, L. L. Marnell, J. Hutt, G. J. Silverman, D. Tran, and T. W. Du-Clos. 2006. Prevention and reversal of nephritis in MRL/lpr mice with a single injection of C-reactive protein. *Arthritis Rheum* 54:325-335.
3a. Siragam, V., A. R. Crow, D. Brinc, S. Song, J. Freedman, and A. H. Lazarus. 2006. Intravenous immunoglobulin ameliorates ITP via activating Fc© receptors on dendritic cells. *Nat Med* 12:688-692.
4a. Marnell, L., C. Mold, and T. W. Du-Clos. 2005. C-reactive protein: ligands, receptors and role in inflammation. *Clin Immunol* 117:104-111.
5a. Marnell, L. L., C. Mold, M. A. Volzer, R. W. Burlingame, and T. W. Du-Clos. 1995. C-reactive protein binds to FcγRI in transfected COS cells. *J Immunol* 155:2185-2193.
6a. Bharadwaj, D., M. P. Stein, M. Volzer, C. Mold, and T. W. Du Clos. 1999. The major receptor for C-reactive protein on leukocytes is Fcy receptor II. *J Exp Med* 190:585-590.

The invention claimed is:

1. A method of treating immune thrombocytopenic purpura (ITP) in a patient in need thereof comprising administering to said patient an effective amount of C-reactive protein (CRP) or a C-reactive protein mutant selected from the group consisting of D112N (SEQ ID NO:2.), D112A (SEQ ID NO: 3), H38R (SEQ ID NO: 4), D169A (SEQ ID NO: 5), Y175L (SEQ ID NO: 6), L176Q (SEQ ID NO: 7) and F66A./E81A (SEQ ID NO: 8.) or mixtures thereof to said patient.

2. The method according to claim 1 comprising administering CRP, C-reactive protein mutant Y175L (SEQ ID NO: 6) or a mixture of CRP and C-reactive protein mutant Y175L to said patient.

3. The method according to claim 1 wherein said CRP or said mutant is administered parenterally to said patient.

4. The method according to claim 1 wherein said CRP or said mutant is administered intravenously to said patient.

5. A method of treating, ameliorating or reducing the occurrence of disease states, conditions or manifestations of ITP in a patient comprising administering to said patient an effective amount of CRP or a C-reactive protein mutant selected from the group consisting of D112N (SEQ ID NO:2.), D112A (SEQ ID NO: 3), H38R (SEQ ID NO: 4), D169A (SEQ ID NO: 5), Y175L (SEQ ID NO: 6), L176Q (SEQ ID NO: 7) and F66A./E81A (SEQ ID NO: 8.) or mixtures thereof to said patient.

6. The method according to claim 5 wherein said method comprises administering an effective amount of CRP, C-reactive protein mutant Y175L (SEQ ID NO: 6) or a mixture of CRP and C-reactive protein mutant Y175L to said patient.

7. The method according to claim 5 wherein said disease state, condition or manifestation of ITP is selected from the group consisting of bleeding, red dots on the skin, red dots on the mouth membranes, purplish mouth membrane areas, bleeding nose, bleeding gum, digestive bleeding, urinary bleeding, brain bleeding and reduced platelet count.

8. The method according to claim 1 comprising administering C-reactive protein mutant Y175L (SEQ ID NO: 6) to said patient.

9. The method according to claim 8 wherein said mutant is administered parenterally to said patient.

10. The method according to claim 8 wherein said mutant is administered intravenously to said patient.

11. The method according to claim 5 comprising administering C-reactive protein mutant Y175L (SEQ ID NO: 6) to said patient.

12. The method according to claim 11 wherein said mutant is administered parenterally to said patient.

13. The method according to claim 11 wherein said mutant is administered intravenously to said patient.

14. The method according to claim 6 comprising administering C-reactive protein mutant Y175L (SEQ ID NO: 6) to said patient.

* * * * *